US009937047B2

(12) United States Patent
Holt et al.

(10) Patent No.: US 9,937,047 B2
(45) Date of Patent: Apr. 10, 2018

(54) SPACER MOLD FOR ORTHOPEDIC IMPLANTS

(71) Applicant: Zimmer, Inc., Warsaw, IN (US)

(72) Inventors: Christopher J. Holt, Warsaw, IN (US); Michael Cordonnier, Encinitas, CA (US); Dimitri Protopsaltis, Memphis, TN (US); William Daniel, Southaven, MS (US); Amber Lenz, Germantown, TN (US); Terrance Strohkirch, Memphis, TN (US); Philip Gilbert, New Baltimore, MI (US)

(73) Assignee: Zimmer, Inc., Warsaw, IN (US)

( * ) Notice: Subject to any disclaimer, the term of this patent is extended or adjusted under 35 U.S.C. 154(b) by 302 days.

(21) Appl. No.: 14/362,845

(22) PCT Filed: Dec. 6, 2012

(86) PCT No.: PCT/US2012/068226
§ 371 (c)(1),
(2) Date: Jun. 4, 2014

(87) PCT Pub. No.: WO2013/086177
PCT Pub. Date: Jun. 13, 2013

(65) Prior Publication Data
US 2014/0348973 A1   Nov. 27, 2014

Related U.S. Application Data

(60) Provisional application No. 61/567,192, filed on Dec. 6, 2011.

(51) Int. Cl.
*A61F 2/36* (2006.01)
*B29C 47/00* (2006.01)
*A61F 2/30* (2006.01)

(52) U.S. Cl.
CPC ............ *A61F 2/36* (2013.01); *B29C 47/0009* (2013.01); *A61F 2/3094* (2013.01);
(Continued)

(58) Field of Classification Search
CPC ................ B29C 33/3828; B29C 33/56; B29C 2033/023; B29C 2945/00; B29C 47/0009;
(Continued)

(56) References Cited

U.S. PATENT DOCUMENTS 4,625,907 A * 12/1986 Mangla ................ B65D 85/324
                                                         206/521.1
6,361,731 B1    3/2002  Smith et al.
(Continued)

FOREIGN PATENT DOCUMENTS

EP      2522310 A1    11/2012
EP      2787928 A1    10/2014
(Continued)

OTHER PUBLICATIONS

"International Application Serial No. PCT/US2012/068226, International Preliminary Report on Patentability dated Mar. 20, 2014", 8 pgs.
(Continued)

*Primary Examiner* — Yogendra N Gupta
*Assistant Examiner* — Emmanuel S Luk
(74) *Attorney, Agent, or Firm* — Schwegman Lundberg & Woessner, P.A.

(57) ABSTRACT

A mold for forming a prosthesis is disclosed. The mold can include a stem portion, a head portion, and a securement assembly. The stem portion and the head portion can be provided in a kit having a variety of different interior dimensions so that a user can select or customize a mold cavity size based on the dimensions of a particular implant site of a patient. While a set of stem portions and head
(Continued)

portions can have interior dimensions of varying sizes, each of the stem portions and each of the head portions can have the same or similar exterior dimensions for attachment using a common securement structure. Related methods are also disclosed.

33 Claims, 29 Drawing Sheets

(52) U.S. Cl.
CPC ............. *A61F 2002/30492* (2013.01); *A61F 2002/30507* (2013.01); *A61F 2002/30616* (2013.01); *A61F 2002/30672* (2013.01); *A61F 2310/00353* (2013.01); *B29C 2945/00* (2013.01)

(58) Field of Classification Search
CPC ....... B29K 2905/08; A61F 2310/00353; A61F 2002/30507; A61F 2002/30492; A61F 2002/30616; A61F 2/3094
See application file for complete search history.

(56) References Cited

U.S. PATENT DOCUMENTS

| | | | | |
|---|---|---|---|---|
| 8,206,143 | B2* | 6/2012 | Hawkins | B28B 23/024 425/214 |
| 8,221,112 | B2* | 7/2012 | McNiven | A61F 2/958 249/111 |
| 8,920,152 | B2* | 12/2014 | Hawkins | 249/161 |
| 2006/0093699 | A1* | 5/2006 | Arakelyan | B29C 49/541 425/541 |
| 2007/0026098 | A1* | 2/2007 | Lemaistre | B29C 33/26 425/170 |
| 2007/0190202 | A1* | 8/2007 | Mie | B29C 49/56 425/541 |
| 2009/0146342 | A1* | 6/2009 | Haney | A61F 2/30942 264/250 |
| 2009/0175978 | A1* | 7/2009 | Hawkins | A61F 2/30 425/214 |
| 2009/0234034 | A1* | 9/2009 | Blanco | B29B 17/0052 521/48 |
| 2010/0276567 | A1* | 11/2010 | MacAlister | F25C 1/22 249/134 |
| 2011/0094059 | A1* | 4/2011 | Sze | B29C 49/48 16/386 |
| 2012/0148703 | A1* | 6/2012 | Duclos | B29C 33/305 425/214 |

FOREIGN PATENT DOCUMENTS

| WO | WO-2009073781 A2 | 6/2009 |
|---|---|---|
| WO | WO-2013086177 A1 | 6/2013 |

OTHER PUBLICATIONS

"International Application Serial No. PCT/US2012/068226, International Search Report dated Feb. 15, 2013", 3 pgs.

"International Application Serial No. PCT/US2012/068226, Response filed Sep. 23, 2013 to Written Opinion dated Feb. 15, 2013", 15 pgs.

"International Application Serial No. PCT/US2012/068226, Written Opinion dated Feb. 15, 2013", 6 pgs.

"International Application Serial No. PCT/US2012/068226, Written Opinion dated Nov. 5, 2013", 7 pgs.

* cited by examiner

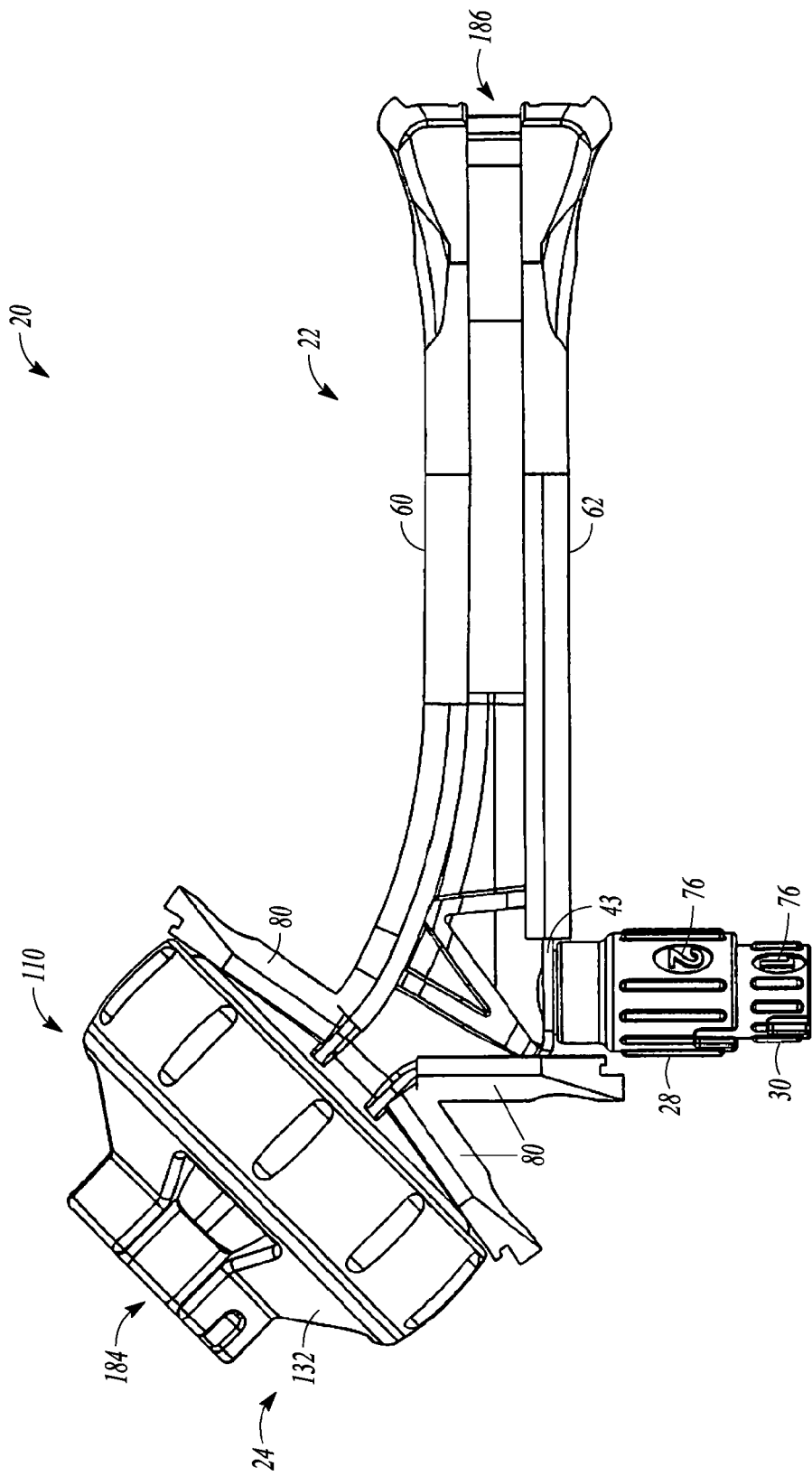

SPACER MOLD FOR ORTHOPEDIC IMPLANTS

CLAIM OF PRIORITY

This patent application is a U.S. National Stage Filing under 35 U.S.C. 371 from International Patent Application Serial No. PCT/US2012/068226 filed Dec. 6, 2012, published on WO 2013/086177A1, which claims the benefit of priority to U.S. Patent Application Ser. No. 61/567,192, filed Dec. 6, 2011, both of which are hereby incorporated by reference herein in their entirety.

TECHNICAL FIELD

This patent document relates to molds for forming orthopedic implants. More particularly, but not by way of limitation, this patent document relates to molds for forming temporary spacer orthopedic implants.

BACKGROUND

It is possible for tissue surrounding orthopedic implants, such as knee or hip implants, to become infected. If necessary, an implant is removed and it can take several weeks or more to adequately treat the infection, during which time an implant site is kept immobile. The implant site immobility can result in shrinkage of the space previously occupied by the implant.

OVERVIEW

To prevent shrinkage of an implant site, a temporary spacer prosthesis (e.g., made of an antibiotic-filled cement) can be used to fill a space occupied by a prior implant while the infection is being cleared from the implant site. Once the temporary spacer prosthesis is positioned, antibiotic can leach out of the spacer prosthesis to treat nearby tissue and prevent further spreading of the infection. Once the infection is cleared, the temporary spacer prosthesis can be replaced with a new, permanent implant.

The present disclosure provides an improved spacer mold for forming a temporary spacer prosthesis. The spacer mold can include a stem portion, a head portion, and a securement assembly. The stem portion and the head portion can be provided in a kit having a variety of different interior dimensions so that a surgeon can select or customize a mold cavity size based on the dimensions of a particular implant site of a patient. While a set of stem portions and head portions can have interior dimensions of varying sizes, each of the stem portions and each of the head portions can have the same or similar exterior dimensions for attachment using a common securement structure.

In one embodiment, the stem portion can include a groove that extends around the periphery of the stem portion to prevent cement seepage from an interior cavity of the spacer mold during injection of cement and hardening of the cement. In another embodiment, the head portion can include a sealing ring attachable into an interior portion of a head securing member. With the sealing ring secured within the head securing member and the head securing member threadingly or otherwise connected to the stem portion, the sealing ring can prevent the head securing member from separating from the head module during a molding process due to the pressure build-up during the filling of the spacer mold and setting of the cement within the head molding chamber. In another embodiment, after a nozzle of a cement gun is removed from a portion of the spacer mold, a plug including a flash preventing post can be inserted within the channel of the port such that the flash preventing post forms a physical barrier in the channel of the port and prevents the formation of any flash in the channel of the port. In another embodiment, if a nozzle of a cement gun is selected by a surgeon or other user that is not sized to connect to the port of the spacer mold, a port adapter is securable to the port so that the nozzle of the cement gun can be properly connected to the port adapter.

In one form thereof, the present disclosure provides a spacer mold for forming a temporary prosthesis, including a stem portion including at least first and second stem members together defining a stem cavity; a securement assembly including a plurality of securement members slidably attachable to the stem members to secure the stem members; and a head portion removably attachable to the stem portion and defining a head cavity.

To better illustrate the prosthetic spacer molds and related kits and methods disclosed herein, a non-limiting list of embodiments is provided here:

In Embodiment 1, a prosthetic mold comprises a stem portion including a first stem member, having a plurality of first engagement members, and a second stem member, having a plurality of second engagement members. The first and second stem members can be configured to engage with one another to define a stem cavity having a cavity circumference. The prosthetic mold can further comprise a plurality of securement members, each configured to slidingly engage at least one of the plurality of first engagement members and at least one of the plurality of second engagement members to secure the first and second stem members to each other.

In Embodiment 2, the prosthetic mold of Embodiment 1 is optionally configured such that the cavity circumference is defined entirely by the first and second stem members.

In Embodiment 3, the prosthetic mold of any one or any combination of Embodiments 1 or 2 is optionally configured such that the plurality of first and second engagement members comprises one of a rail or a track, and the plurality of securement members comprises the other one of a rail or a track.

In Embodiment 4, the prosthetic mold of Embodiment 3 is optionally configured such that the plurality of first and second engagement portions comprises a rail and the plurality of securement members comprises a track.

In Embodiment 5, the prosthetic mold of Embodiment 3 is optionally configured such that the track includes a locking lip and an undercut.

In Embodiment 6, the prosthetic mold of any one or any combination of Embodiments 1 or 2 is optionally configured such that the plurality of first engagement members comprises a plurality of spaced, substantially half-cylindrical members opened in a first direction, and the plurality of second engagement members comprises a plurality of spaced, half-cylindrical members opened in a second direction opposite the first direction. When the first and second stem members are mated, the half-cylindrical members of the first and second stem members cooperate to define a substantially continuous channel for engaging one of the plurality of securement members.

In Embodiment 7, the prosthetic mold of Embodiment 6 is optionally configured such that the plurality of securement members comprises a pin configured to be received in the substantially continuous channel.

In Embodiment 8, the prosthetic mold of any one or any combination of Embodiments 1-7 is optionally configured such that the first and second stem members each further comprise a head chamber portion configured to form a lower portion of a head cavity.

In Embodiment 9, the prosthetic mold of Embodiment 8 is optionally configured such that a first head chamber portion and a second head chamber portion each comprise a plurality of head chamber engagement portions configured to slidably engage a corresponding plurality of the securement members.

In Embodiment 10, the prosthetic mold of Embodiment 8 optionally further comprises a head portion removably attachable to the head chamber portion.

In Embodiment 11, the prosthetic mold of Embodiment 10 is optionally configured such that the head chamber portion of each of the first and second stem members includes a threaded wall, and the head portion includes a head module, having a concave arcuate interior surface defining an upper portion of the head cavity and disposed between the head securing member and the head chamber portion, and a head securing member, configured to engage the threaded wall to secure the head module to the head chamber portion.

In Embodiment 12, the prosthetic mold of claim 11, is optionally configures such that the head module comprises at least two head module members.

In Embodiment 13, the prosthetic mold of any one or any combination of Embodiments 1-12 is optionally configured such that the stem portion further comprises a port in communication with the stem cavity.

In Embodiment 14, the prosthetic mold of any one or any combination of Embodiments 1-13 is optionally configured such that the first and second stem members each further comprise a cooperating seal portion.

In Embodiment 15, the prosthetic mold of Embodiment 14 is optionally configured such that the cooperating seal portion of the first stem member comprises one of a projection or an abutment, and the cooperating seal portion of the second stem member comprises the other one of a projection or an abutment.

In Embodiment 16, the prosthetic mold of any one or any combination of Embodiments 1-15 is optionally configured such that each one of the plurality of first engagement members is disposed in a like position or in mirror image to a corresponding one of the plurality of second engagement members.

In Embodiment 17, a prosthetic mold comprises a stem portion, extending from a proximal end to a distal end, including a first stem member and a second stem member configured to mate to each other to cooperatively define a stem cavity. The first stem member can have a plurality of first engagement members, and the second stem member can have a plurality of second engagement members. Each one of the plurality of first engagement members can be configured to slidably engage each one of the plurality of second engagement members to secure the first and second stem members to each other.

In Embodiment 18, the prosthetic mold of Embodiment 17 is optionally configured such that the plurality of first engagement members comprises a plurality of spaced apertures, and the plurality of second engagement members comprises a plurality of spaced projections configured to be received within the plurality of apertures.

In Embodiment 19, the prosthetic mold of Embodiment 18 is optionally configured such that the plurality of spaced projections slidably engages the plurality of spaced apertures to form a snap-fit arrangement.

In Embodiment 20, the prosthetic mold of any one or any combination of Embodiments 17-19 is optionally configured such that the first and second stem members each further comprise a head chamber portion, configured to form a lower portion of a head cavity, at the proximal end.

In Embodiment 21, the prosthetic mold of Embodiment 20 is optionally configured such that a first head chamber portion comprises a plurality of spaced apertures, and a second head chamber portion comprises a plurality of spaced projections configured to be received within the plurality of apertures.

In Embodiment 22, the prosthetic mold of Embodiment 20 optionally further comprises a head portion removably attachable to the head chamber portion. The head portion can include a head adapter and a head member. The head member can have an arcuate interior surface and defining an upper portion of the head cavity.

In Embodiment 23, the prosthetic mold of Embodiment 22 is optionally configured such that the head chamber portion of the first and second stem members includes one of spaced projections or spaced apertures, and the head adapter includes the other one of spaced projections or spaced apertures. The spaced apertures can be configured to receive the spaced projections to secure the head adapter to the head chamber portion.

In Embodiment 24, the prosthetic mold of Embodiment 23 is optionally configured such that the head adapter further comprises a plurality of radially spaced notches, and the head member further comprises a plurality of radially spaced flanges configured to be received within the plurality of notches to secure the head member to the head adapter.

In Embodiment 25, the prosthetic mold of Embodiment 24 is optionally configured such that the spaced projections form a snap-fit or an interference fit with the spaced apertures, and the spaced flanges form a snap-fit or an interference fit with the spaced notches.

In Embodiment 26, the prosthetic mold of any one or any combination of Embodiments 17-25 is optionally configured such that the stem portion further comprises a port, in communication with the stem cavity, disposed at the distal end.

In Embodiment 27, the prosthetic mold of any one or any combination of Embodiments 17-26 is optionally configured such that the first and second stem members each further comprise a cooperating seal portion.

In Embodiment 28, the prosthetic mold of Embodiment 27 is optionally configured such that the cooperating seal portion of the first stem member comprises one of a projection or an abutment, and the cooperating seal portion of the second stem member comprises the other one of a projection or an abutment.

In Embodiment 29, a prosthetic mold kit comprises a plurality of stem molds and a securement member assembly. Each one of the plurality of stem molds can have a stem portion including a first stem member, having a first engagement member, and a second stem member, having a second engagement member, configured to engage with one another to define a stem mold exterior and a stem mold interior cavity. The stem mold exterior dimension can be substantially the same for each one of the plurality of stem molds, and the interior cavity dimension can be different for each one of the plurality of stem molds. The securement member assembly can be configured to simultaneously engage the first engagement member and the second engagement member of any one of the plurality of stem molds to secure the first and second stem members to each other.

In Embodiment 30, the prosthetic mold kit of Embodiment 29 is optionally configured such that the exterior dimension is a stem portion length and the interior dimension is an interior cavity length.

In Embodiment 31, the prosthetic mold kit of Embodiment 29 is optionally configured such that the exterior dimension is a stem portion width and the interior dimension is an interior cavity width.

In Embodiment 32, the prosthetic mold kit of claim 29 optionally includes a plurality of head molds. Each one of the plurality of head molds can have a concave arcuate interior surface defining an upper portion of a head cavity. The any one of the plurality of head molds is configured to be attached to any one of the plurality of stem molds.

In Embodiment 33, the prosthetic mold kit of claim 32, is optionally configured such that the head mold exterior includes at least one dimension that is substantially the same for each one of the plurality of head molds, and the head cavity includes at least one dimension that is different for each one of the plurality of head molds.

In Embodiment 34, a method of securing components of a prosthetic mold comprises providing or obtaining a first stem member and a second stem member configured to each with one another to define an interior cavity, the first and second stem members each having an medial engagement portion and a lateral engagement portion; providing or obtaining a plurality of securement members; mating the first stem member to the second stem member; slidably engaging one of the plurality of securement members with one of the medial or lateral engagement portions of each one of the first and second stem members; and slidably engaging another one of the plurality of securement members with the other one of the medial or lateral engagement portions of each one of the first and second stem members.

In Embodiment 35, the prosthetic spacer molds and related kits and methods of any one (or portion of any one) or any combination of Embodiments 1-30 is optionally configured such that all elements or options recited are available to use or select from.

These and other examples and features of the present prosthetic spacer molds and related kits and methods will be set forth in part in the following Detailed Description. This Overview is intended to provide non-limiting examples of the present subject matter—it is not intended to provide an exclusive or exhaustive explanation. The Detailed Description below is included to provide further information about the present prosthetic spacer molds and related kits and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present patent document.

FIG. 9A: illustrates an anterior/posterior elevation view of the spacer mold of FIG. 1.

DETAILED DESCRIPTION

The present disclosure provides a spacer mold for forming a temporary prosthesis. The spacer mold can be releasably connectable to a nozzle of an injector, such as a cement gun, that uses pressurized cartridges of a curable material, for example, such as Zimmer's Power-Flo® Bone Cement Injector described in the "Zimmer® Bone Cement and Accessories" brochure, ©2006, published by Zimmer, Inc., the entire disclosure of which is hereby expressly incorporated herein by reference. The injector can eject curable material from a cartridge, such as high-strength, high-viscosity poly-methyl-methacrylate (PMMA). This includes materials such as Palacos® R+G High Viscosity Bone Cement and any other similar material suitable for forming an orthopedic implant or prosthesis. As used herein, the terms "curable material" and "cement" can be used interchangeably and such terms generally refer to any curable or hardening material suitable for forming spacers or orthopedic prosthesis components. An antibiotic, such as gentamicin and/or clidamycin, to treat infection in the bone and/or tissue surrounding the implant site can be incorporated in the cement to be injected into a spacer mold in accordance with the present disclosure.

Figure 12:
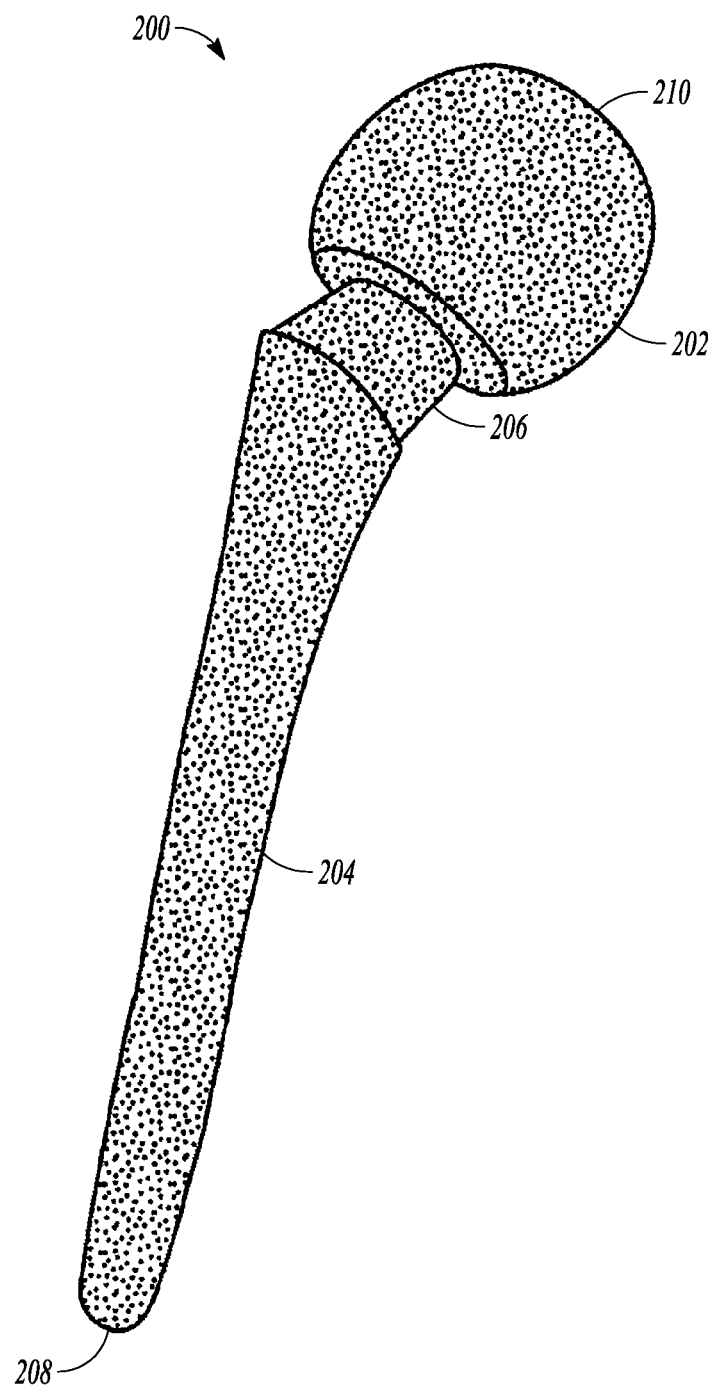
FIG. 12: illustrates a perspective view of a spacer formed by the spacer mold of FIG. 1 in accordance with the present disclosure.

An exemplary spacer 200, shown in FIG. 12, is formed by a spacer mold in accordance with the present disclosure. Spacer 200 includes spacer head 202 connected to, or integrally formed with, spacer stem 204. Spacer neck 206 connects spacer head 202 to spacer stem 204 to generally correspond to the shape of the articulating portion of a bone, and spacer 200 extends between distal end 208 and proximal end 210. Although exemplified in the various drawings as a hip spacer, a spacer mold in accordance with the present disclosure can also be sized and shaped to form other temporary orthopedic implants or spacers, such as, but not limited to, a temporary tibial spacer, a temporary femoral spacer, or any other temporary spacer implant.

Referring to FIGS. 1-3 and 12, spacer mold 20 generally includes stem portion 22 used to form spacer stem 204 and neck 206, head portion 24 used to form spacer head 202, and a securement member assembly for securing the components of spacer mold 20 together. The securement member assembly includes at least a first stem securement member 60, a second stem securement member 62, and a plurality of head chamber securement members 80. Spacer mold 20 can also include port adapter 28 and pug 30 as will be further described below.

Figure 4:
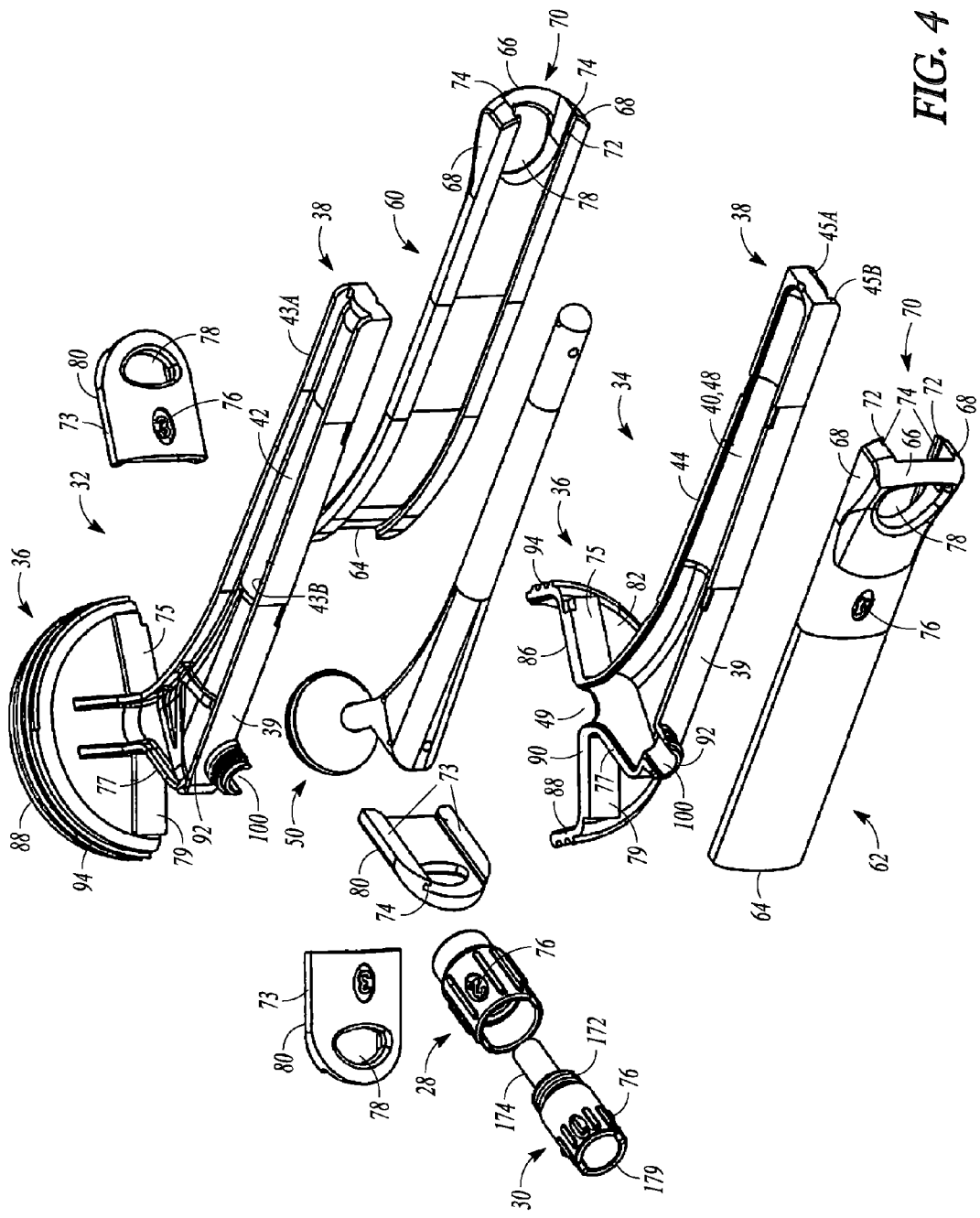
FIG. 4: illustrates an exploded perspective view of a spacer mold in accordance with the present disclosure.

In one embodiment, referring to FIG. 4, stem portion 22 includes corresponding first and second stem members 32, 34 that can be mirror images of each other. In alternative embodiments, first and second stem members 32, 34 can have different geometries and/or shapes. First stem member 32 and second stem member 34 each include a proximal end 36, a distal end 38, and an intermediate portion 39 between proximal end 36 and distal end 38. First and second stem members 32, 34 each include respective longitudinal walls 42, 44 extending from proximal end 36 to distal end 38 of first and second stem members 32, 34.

First and second stem members 32, 34 are configured to mate and cooperatively define a main, longitudinally extending space or cavity 40 (FIGS. 4 and 11) between first and second stem members 32, 34. First and second stem members 32, 34 each form respective aligning symmetrical stem grooves 46, 48 and neck grooves 47, 49 that align to form stem portion of cavity 40 (in FIGS. 4 and 11, only stem groove 48 and neck groove 49 on second stem member 34 are shown in FIG. 4). Referring to FIG. 12, stem 204 and neck 206 of spacer 200 are formed in stem cavity 40 of first and second stem members 32, 34. Referring to FIG. 4, wall exterior surfaces of longitudinal walls 42, 44 include at least one protruding rail 43, 45 extending at least a portion of the length of the longitudinal walls 42, 44, the protruding rails 43, 45 configured to be received, respectively, within first and second stem securement members 60, 62, as described below.

Figure 11:
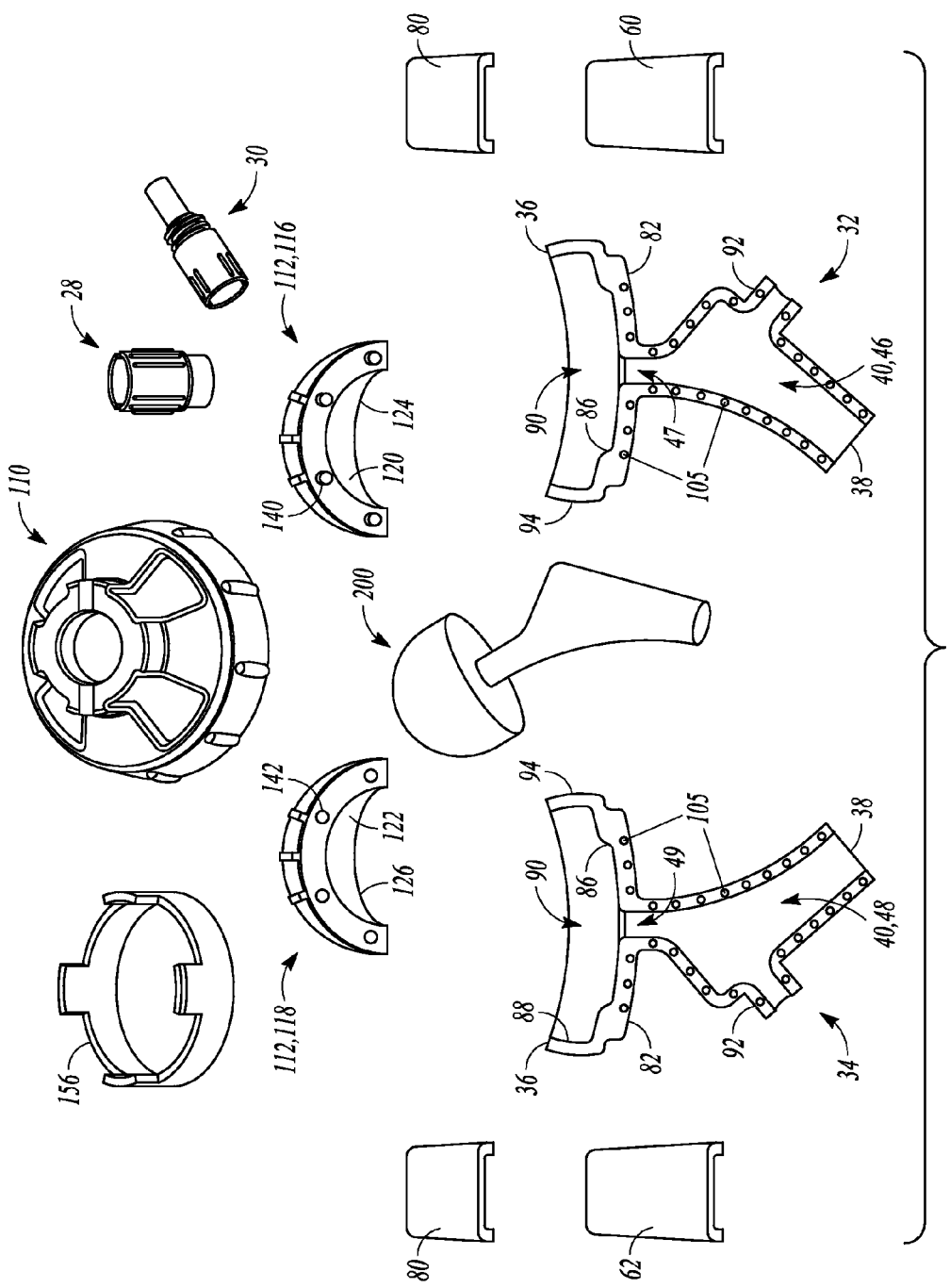
FIG. 11: illustrates an exploded perspective view of a spacer mold in accordance with the present disclosure.

Referring to FIGS. 4 and 11, proximal end 36 of each of stem members 32, 34 includes corresponding widened sections defining a lower portion of head molding chamber 90. Bottom walls 82 extend radially outward from respective stem members 32, 34 at neck grooves 47, 49. Bottom walls 82 of stem members 32, 34 extend longitudinally or upwardly to form cylindrical wall 88 of each of stem members 32, 34. Cylindrical wall 88 and bottom wall 82 of stem members 32, 34 are configured to mate and cooperatively form a lower portion of head molding chamber 90. Cylindrical wall 88 of stem members 32, 34 includes exterior threaded portion 94 for securing head securing member 110 thereto to form head portion 24, as will be described in more detail below.

Referring to FIG. 4, in one embodiment intermediate section 39 of respective first and second stem members 32, 34 includes port portion 92. Respective port portion 92 of first and second stem members 32, 34 are configured to mate and cooperatively form port 100, with first and second stem members 32, 34 aligned and secured together with the securement member assembly which includes a plurality of stem securement members 60, 62 and a plurality of head chamber securement members 80. Port portion 92 can include port portion rails 77 for attachment of securement member 80 to reinforce attachment for first and second stem members 32, 34 at port 100. In other embodiments, additional securement members and/or other attachment means can be disposed at or adjacent to port portion 92, such as apertures 105 in walls 42, 44 and/or rails 43, 45 of first and second stem members 32, 34 (shown in FIG. 11) that can receive pins or screws to further secure stem members 32, 34 adjacent to the port 100. In other embodiments, port 100 can itself be formed entirely within either first stem member 32 or second stem member 34. Port 100 provides access to cavity 40 of spacer mold 20 to receive cement injected from a cement gun or other injector of pressurized, curable material. Cement is provided from a cartridge of a cement gun at a pressure sufficient to spread cement to substantially fill the interior of spacer mold 20. Specifically, the cement fills the entirety of cavity 40 from proximal end portion 38 to intermediate section 39 forming spacer stem 204 (FIG. 12), the cement also fills the entirety of neck groove 47, 49 of cavity 40 forming neck 206 of spacer 200 (FIG. 12), and the cement fills the head molding chamber 90 within head portion 24 as will be described in more detail below forming spacer head 202 (FIG. 12). Stem securement members 60, 62 can be of any length configured to secure at least a portion of stem members 32, 34.

Port 100 is sufficiently rigid to remain connected to the cement gun while the cement is injected under relatively high pressure, such as, for example, at approximately 300 psi to 350 psi. The remainder of spacer mold 20 also has sufficient rigidity to receive the cement under high pressure without compromising the effectiveness of spacer mold 20 and unintentional disconnect of an injector from port 100. In other words, port 100 and the remainder of spacer mold 20 will not break, split, or crack when the pressurized cement is received under pressure within spacer mold 20. For these purposes, in one embodiment, high density polyethylene is used to form spacer mold 20.

Figure 6:
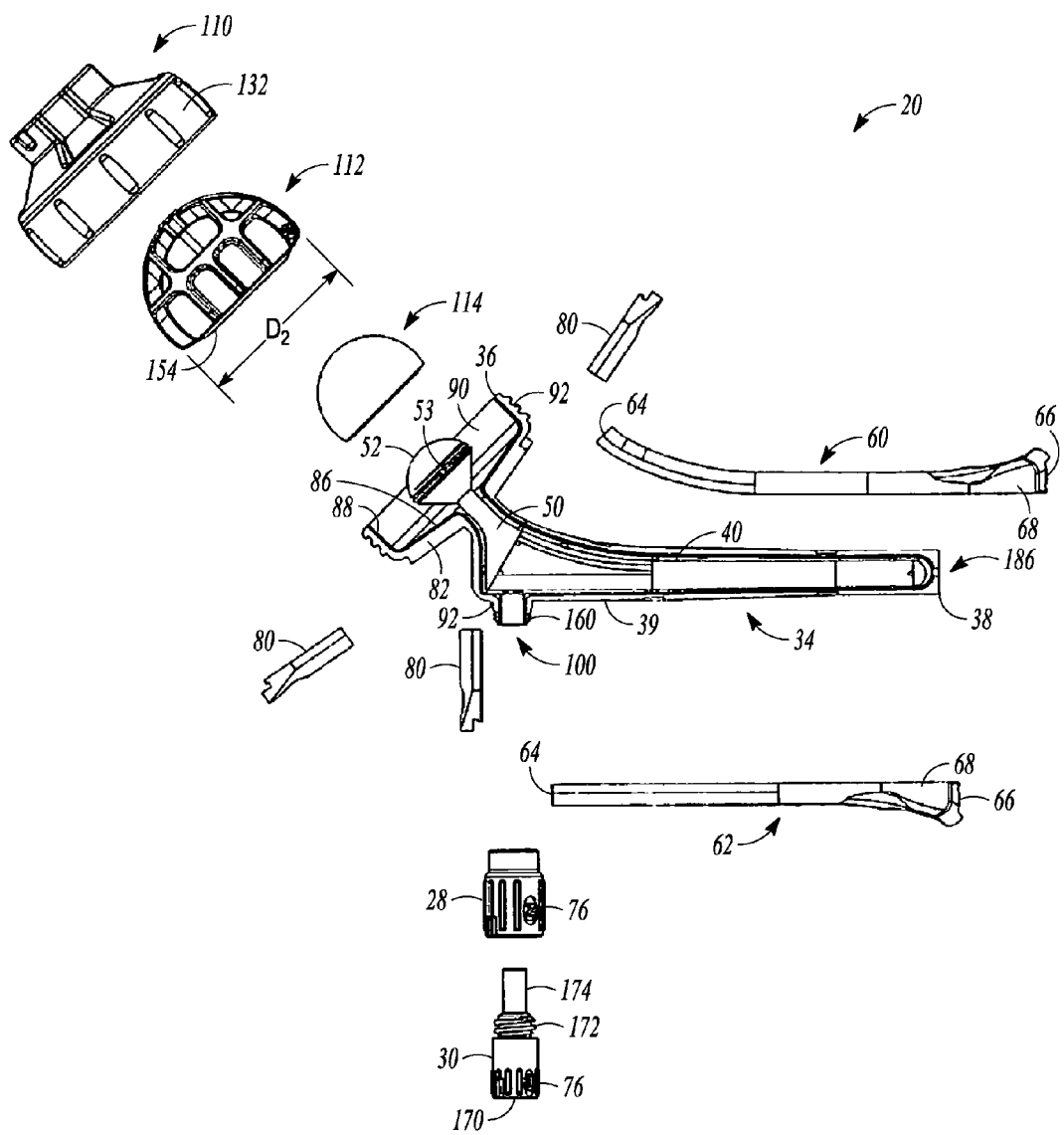
FIG. 6: illustrates an exploded perspective view of a spacer mold in accordance with the present disclosure.
Figure 8A:
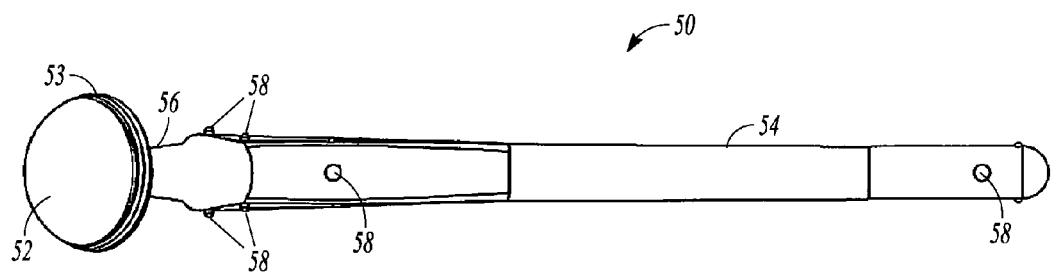
FIG. 8A: illustrates a medial view of a reinforcing bar of the spacer mold of FIG. 4.
Figure 8B:
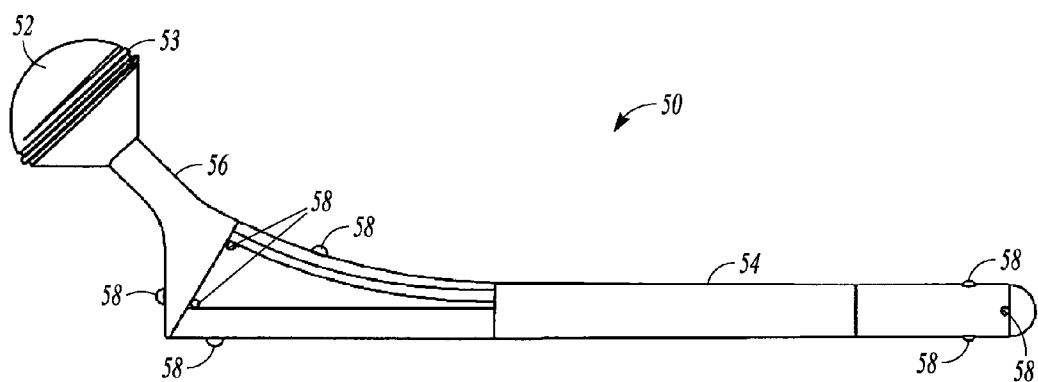
FIG. 8B: is an anterior/posterior elevation view of the reinforcing bar of FIG. 8A.
Figure 8C:
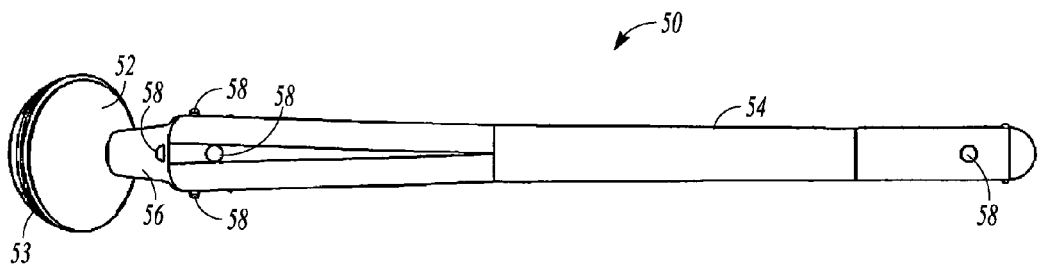
FIG. 8C: illustrates a lateral elevation view of the reinforcing bar of FIG. 8A.
Figure 8D:
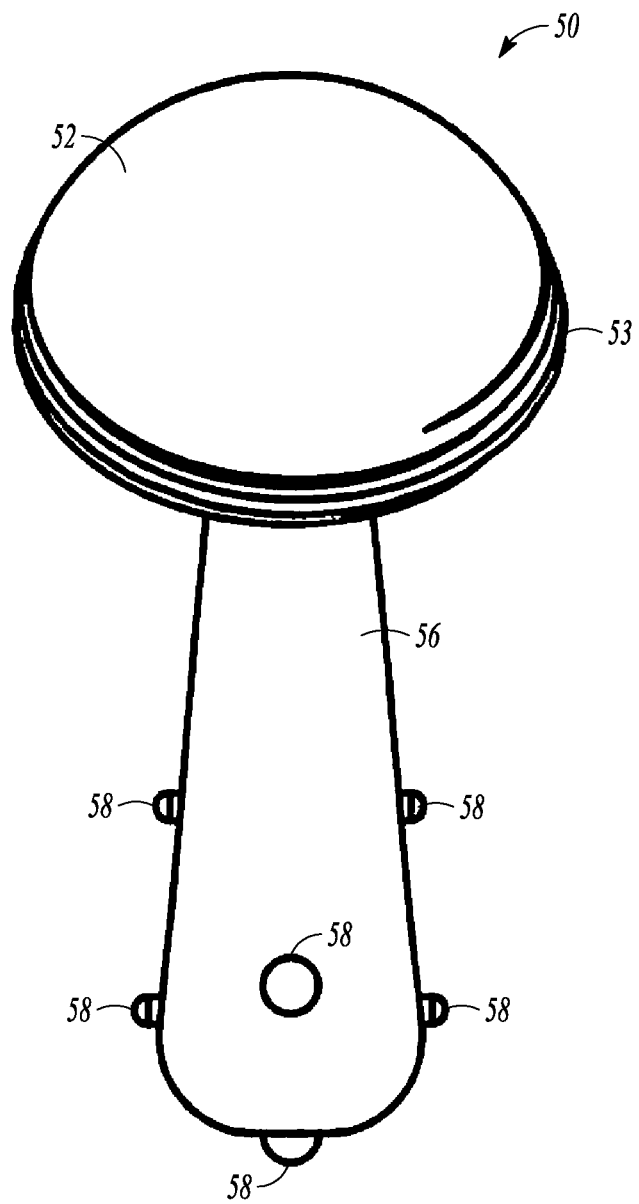
FIG. 8D: illustrates a proximal elevation view of the reinforcing bar of FIG. 8A.
Figure 8E:
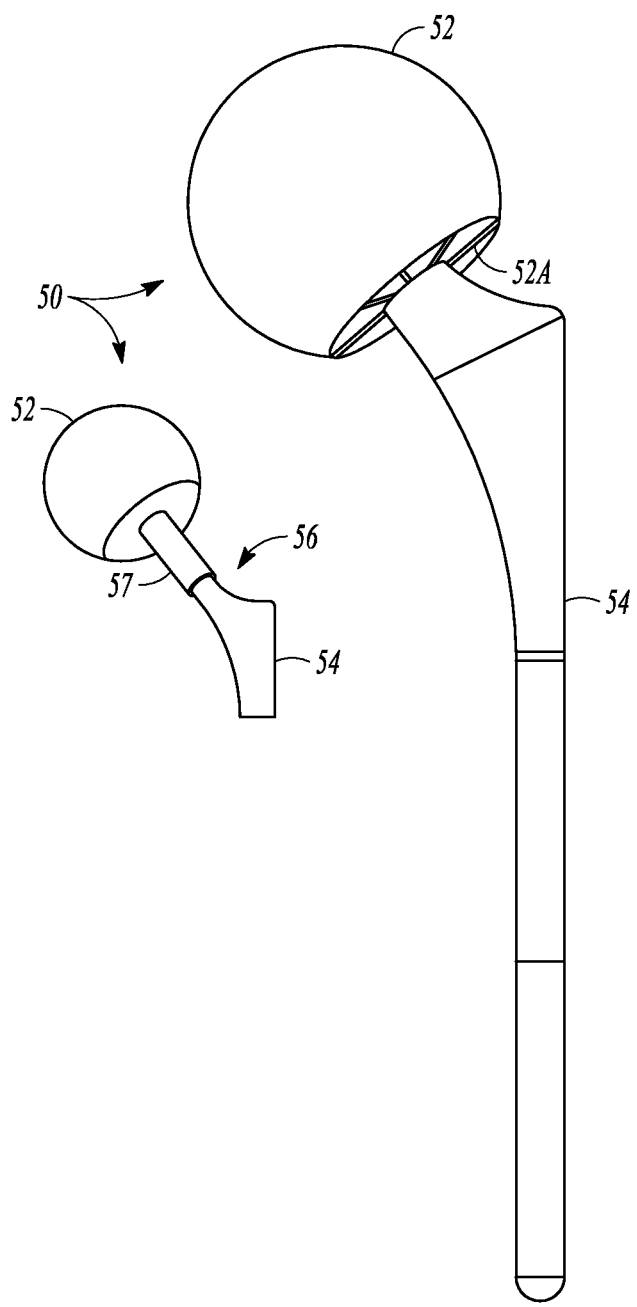
FIG. 8E: illustrates an embodiment of a modular reinforcing bar and a reinforcing bar head having one or more flow channels.

Referring to FIGS. 8A-8E, reinforcing bar 50 includes reinforcing bar head 52 which includes threaded portion 53 for attachment of head bridge member 114 (FIG. 6), reinforcing bar stem 54, reinforcing bar neck 56 which connects reinforcing bar head 52 to reinforcing bar stem 54, and reinforcing bar projections 58 spaced along reinforcing bar 50. Reinforcing bar 50 can be made of any rigid material or combination of materials, for example, bone cement, metals or alloys, such as Co—Cr, Ti or alloys thereof, or a combination of bone cement and metals or metal alloys. Reinforcing bar 50 has a reinforcing bar stem 54 and generally widened disc-shaped head 52 for extending into, and filling a portion of, head molding chamber 90 of spacer mold 20, as shown in FIG. 6. In one embodiment, reinforcing bar 52 head has flow channels 52A on or more surfaces (as shown in FIG. 8E) to direct the flow of cement. In another embodiment, as shown in FIG. 8E, reinforcing bar 50 is modular, for example having modular stem 54, neck 56 and head 52 components that are configured to be attached or fitted together to form reinforcing bar 50. For example, reinforcing bar head 52 can be modular and made available in a variety of sizes. In such an embodiment, reinforcing bar head 52 could be secured to a reinforcing bar stem 54 via reinforcing bar neck 56 by connection 57, such as by a press-fit, an interference fit, a weld, a locking taper, a threaded connection, or similar securement method well known in the art, as shown in FIG. 8E. A modular reinforcing bar assembly can reduce the overall cost associated with reinforcing bar 50 by reducing unit costs, manufacturing costs, and/or machining costs.

Figure 10A:
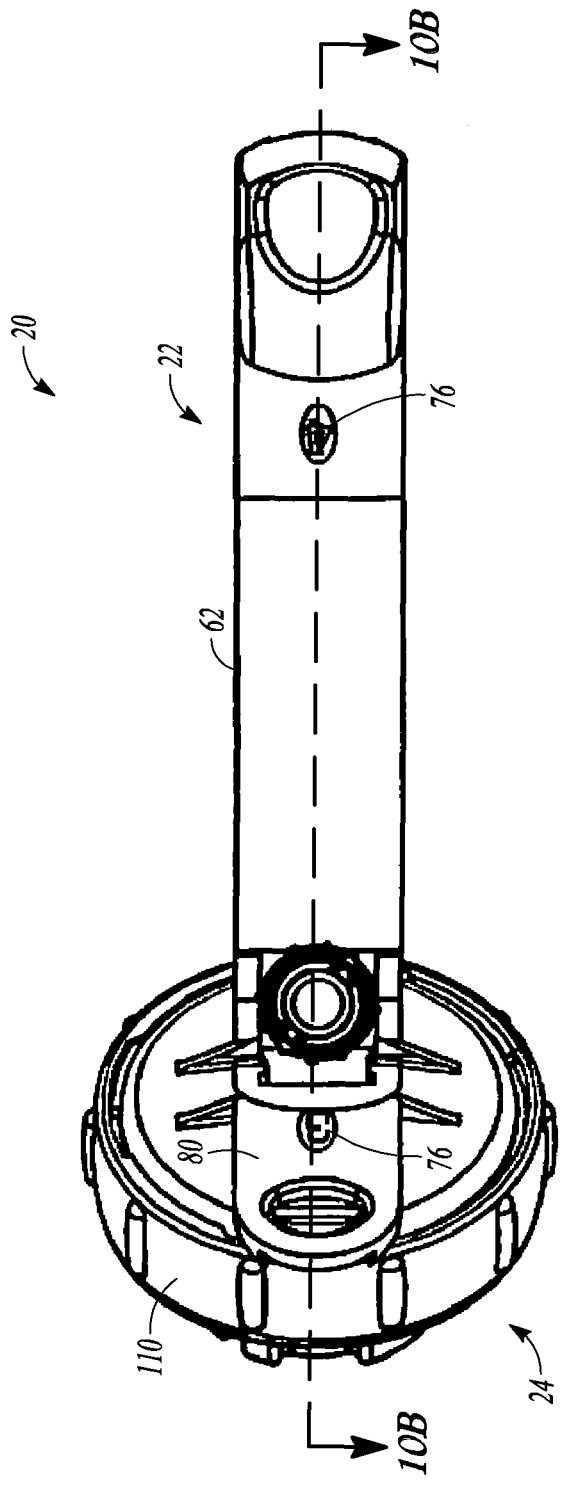
FIG. 10A: illustrates a lateral elevation view of the spacer mold of FIG. 1.
Figure 10B:
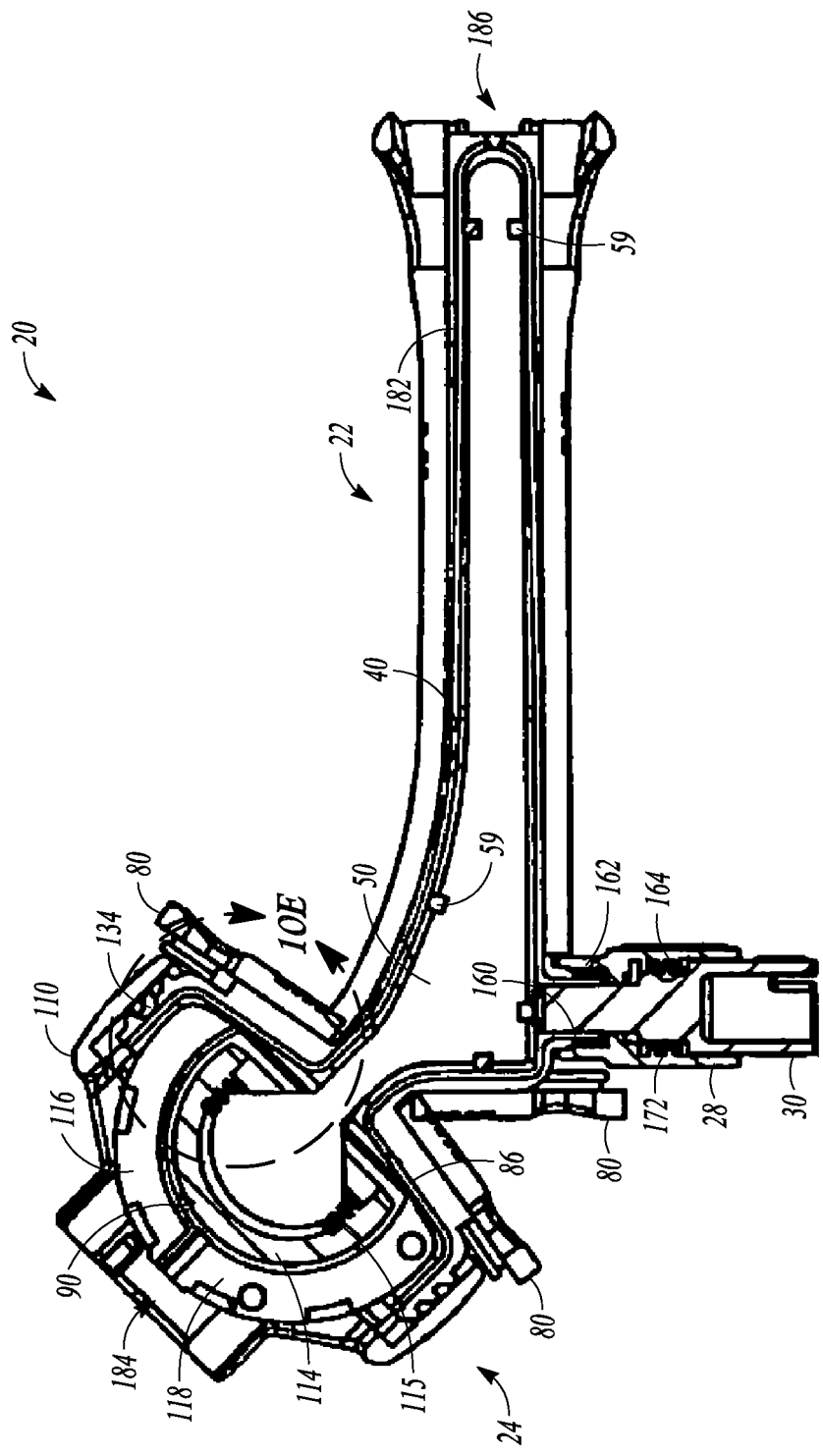
FIG. 10B: illustrates a cross-sectional view taken along line 10B-10B of FIG. 10A.

Referring to FIGS. 4, 6 and 10B, cavity 40 defined between stem members 32, 34 can receive reinforcing bar 50 (FIGS. 8A-8E). In this manner, reinforcing bar 50 is embedded within a spacer 200 (FIG. 12) when spacer 200 is formed. Reinforcing bar 50 provides a weight bearing member within spacer 200 and can be used to provide rigidity and strengthen spacer 200 and reduce the amount of cement material necessary to fill spacer mold 20 to form spacer 200. In one embodiment, to embed reinforcing bar 50 in spacer 200 (FIG. 12), reinforcing bar 50 is placed within spacer mold 20 upon assembly of spacer mold, and is spaced from the interior surface of stem members 32, 34 defining cavity 40 so that cement can generally spread to all areas between stem members 32, 34 and reinforcing bar 50 during the filling process. For this purpose, reinforcing bar projections 58 extend outwardly from reinforcing bar 50 to engage the interior surface of stem members 32, 34 with reinforcing bar 50 positioned in cavity 40. In an alternative embodiment, protrusions 59 can be separate from reinforcing bar 50 and can extend from the interior surface of stem members 32, 34 to hold reinforcing bar 50 in a spaced position in cavity 40. In one embodiment, at least one reinforcing bar projection 58 extends from reinforcing bar 50 and engages at least one corresponding protrusion 59 (FIG. 10B) extending from the interior surface of stem members 32, 34 so that reinforcing bar 50 is both centered away from the interior surface of stem members 32, 34 and is secured longitudinally, laterally, and/or rotationally relative to stem members 32, 34.

Referring to FIGS. 4, 6, and 10B, in one embodiment, reinforcing bar 50 is positioned within cavity 40 of spacer mold 20 such that reinforcing bar stem 54 is positioned between stem grooves 46, 48 of stem members 32, 34 and reinforcing bar neck 56 is positioned within respective neck grooves 47, 49 of stem members 32, 34 with reinforcing bar head 52 protruding from bottom 86 of head molding chamber walls 82 and into head molding chamber 90. Additionally, reinforcing bar 50 is generally spaced from the interior surface of stem members 32, 34 defining cavity 40, as discussed above.

With reinforcing bar 50 positioned in spacer mold 20, the securement member assembly, including first and second stem securement members 60, 62 and head chamber securement members 80, can be removably attached to stem members 32, 34 to secure stem members 32, 34 to each other to assemble spacer mold 20. The securement member assembly can be quickly and easily secured to, and removed from, stem members 32, 34 to provide a surgeon with a convenient, quick, and clean system for forming temporary spacer implants during a surgical procedure.

In one embodiment, referring to FIG. 4, first and second stem securement members 60, 62 each include superior end 64, opposing inferior end 66, and two opposing side walls 68 extending the length of stem securement members 60, 62 from superior end 64 to inferior end 66. Side walls 68 define notch 70 therebetween. Each side wall 68 includes locking lip 72 extending from a respective side wall 68 and an undercut 74 disposed below locking lip 72. In one embodiment, securement members 60, 62, 80 each include indicia 76 disposed on an exterior surface to describe the order of disassembly of spacer mold 20 as will be discussed below. In another embodiment, one or more of securement members 60, 62, 80 include removal aperture 78 which can be grasped for quickly and easily removing securement members 60, 62, 80 from stem members 32, 34. In one embodiment, head chamber securement members 80 have similar corresponding parts as first and second stem securement members 60, 62 and are secured to stem members 32, 34 in a similar manner as first and second stem securement members 60, 62 as discussed below. For example, in one embodiment, head chamber securement members 80 include locking lips 73 and undercut 74 for slidably engaging rails 75, 79 of head molding chamber walls 82 and port portion rails 77 of respective first and second stem members 32, 34.

Figure 1:
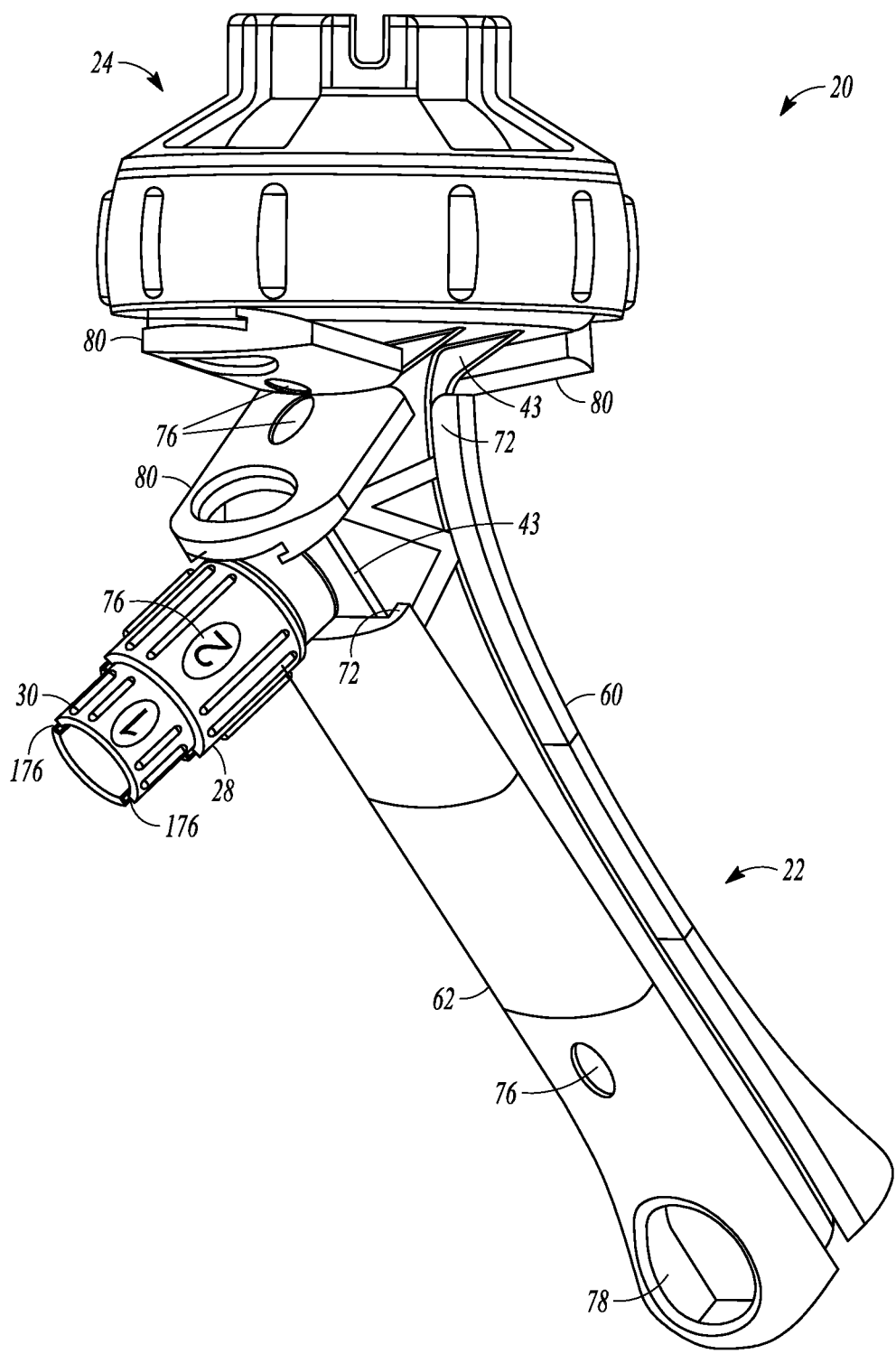
FIG. 1: illustrates a perspective view of a spacer mold in accordance with the present disclosure.

To secure first and second stem members 32 and 34 together using first and second stem securement members 60, 62, opposing locking lips 72 at superior end 64 of stem securement members 60, 62 are positioned over respective protruding rails 43, 45 at distal end 38 of stem members 32, 34 such that respective protruding rails 43, 45 of stem members 32, 34 are received within respective undercuts 74 of first and second stem securement members 60, 62 as shown in FIG. 1. First, locking lips 72 at superior end 64 of first stem securement member 60 are positioned over protruding rails 43A, 45A at distal end 38 of respective first and second stem members 32, 34 such that respective protruding rails 43A, 45A of first and second stem members 32, 34 are received within respective undercuts 74 of first stem securement member 60. Next, first stem securement member 60 is slid onto first and second stem members 32, 34 from their respective distal end 38 to proximal end 36 until the extent of first stem securement member 60 is secured over rails 43A, 45A of first and second stem members 32, 34 as shown in FIG. 1. With first stem securement member 60 secured to stem members 32, 34, second stem securement member 62 is secured to the opposite side of stem members 32, 34, via protruding rails 43B, 45B of first and second stem members 32, 34 in the same manner described above with respect to first stem securement member 60, as shown in FIG. 1. Locking lips 72 at superior end 64 of second stem securement member 62 are positioned over protruding rails 43B, 45B at distal end 38 of respective first and second stem members 32, 34 such that respective protruding rails 43B, 45B of first and second stem members 32, 34 are received within respective undercuts 74 of second stem securement member 62. Next, second stem securement member 62 is slid onto first and second stem members 32, 34 from their respective distal end 38 to proximal end 36 until the extent of second stem securement member 62 is secured over rails 43B, 45B of first and second stem members 32, 34 as shown in FIG. 1. In one embodiment, first and second stem securement members 60, 62 are slid onto protruding rails 43, 45 of respective first and second stem members 32, 34 until a stop (not shown) disposed at inferior end 66 of first and second stem securement members 60, 62 abuts distal end 38 of respective first and second stem members 32,34.

Figure 2:
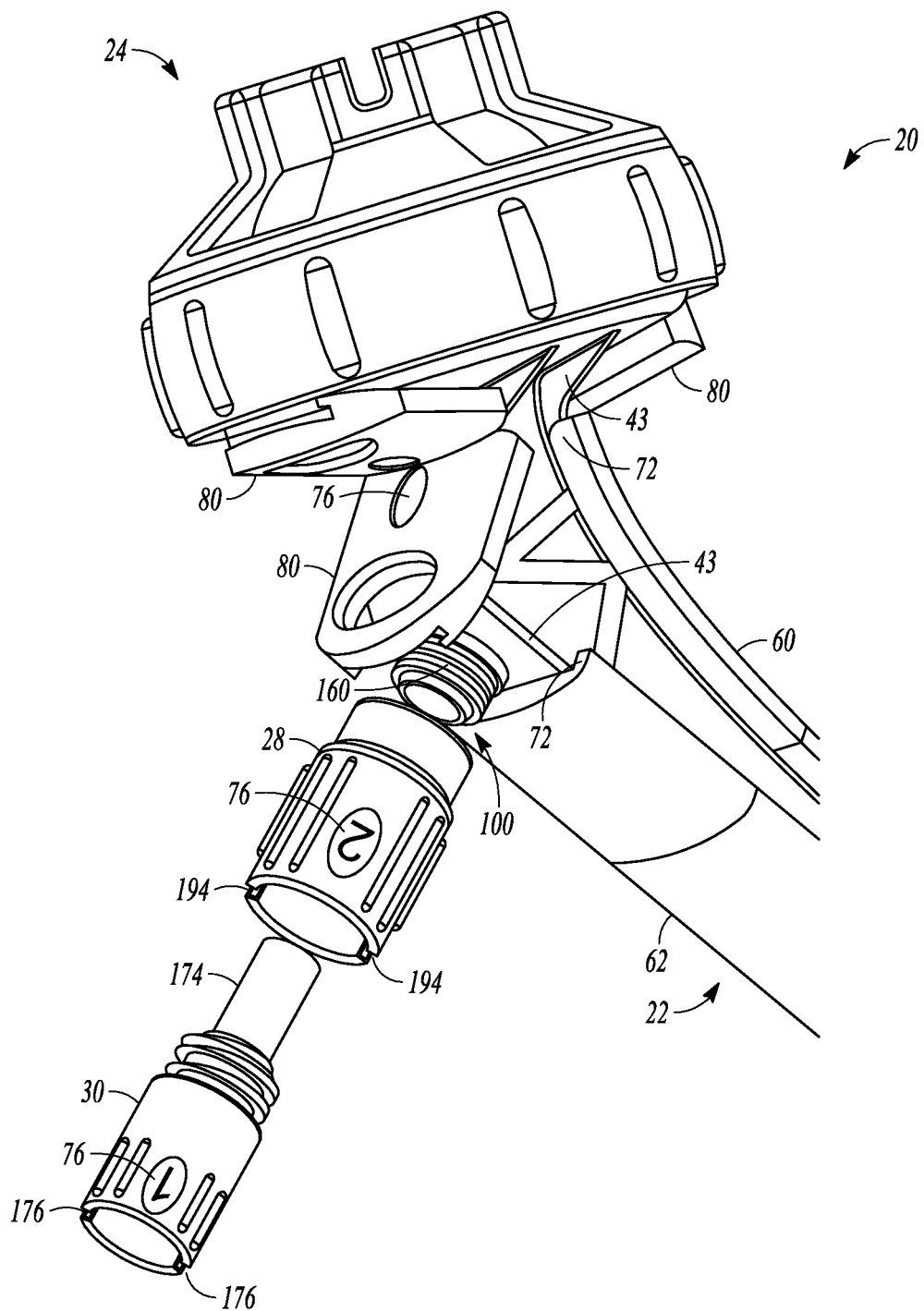
FIG. 2: illustrates a perspective view of the spacer mold of FIG. 1 with a port adapter and a plug shown exploded from a port of the spacer mold.
Figure 5:
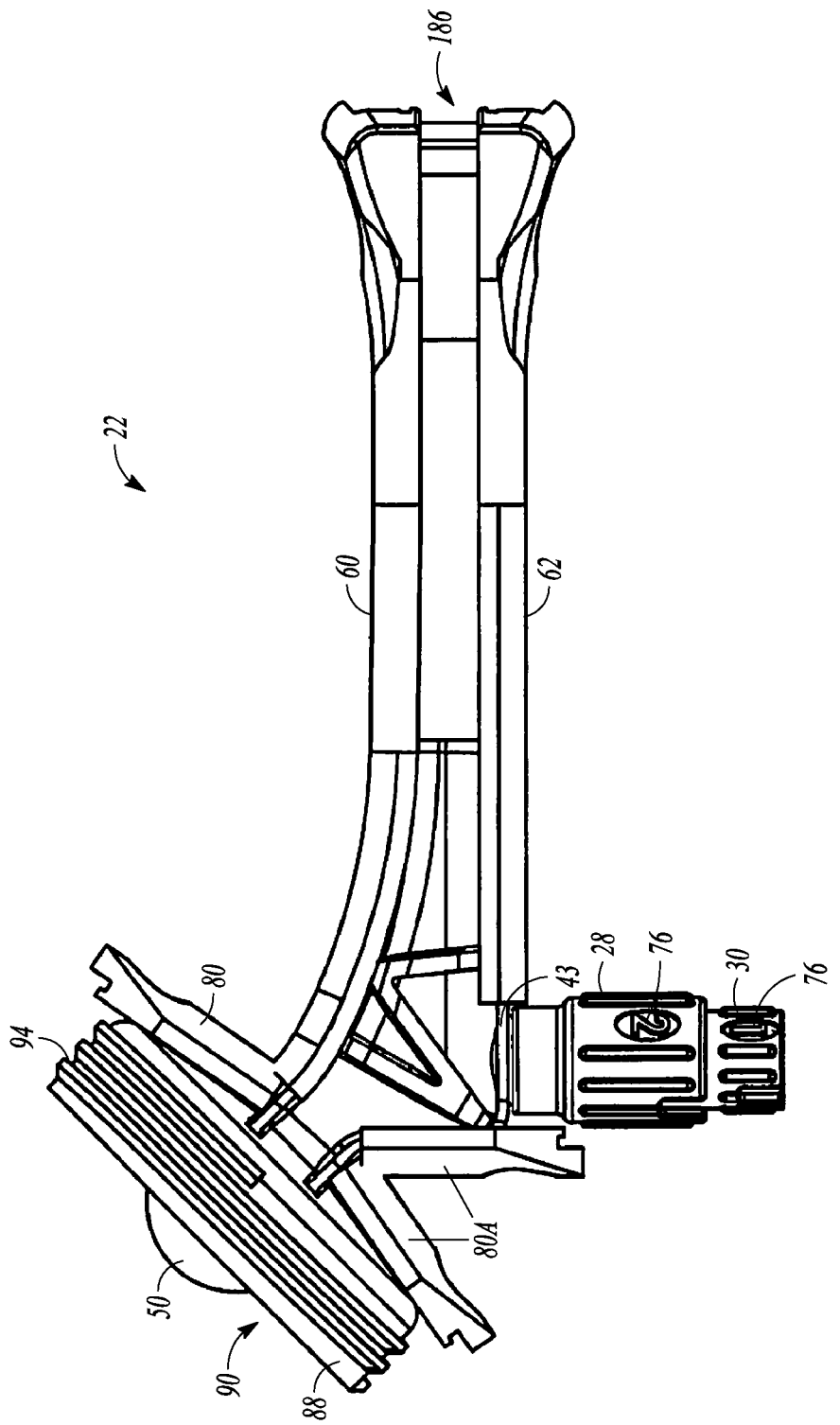
FIG. 5: illustrates an assembled elevation view of the spacer mold of FIG. 4.
Figure 9B:
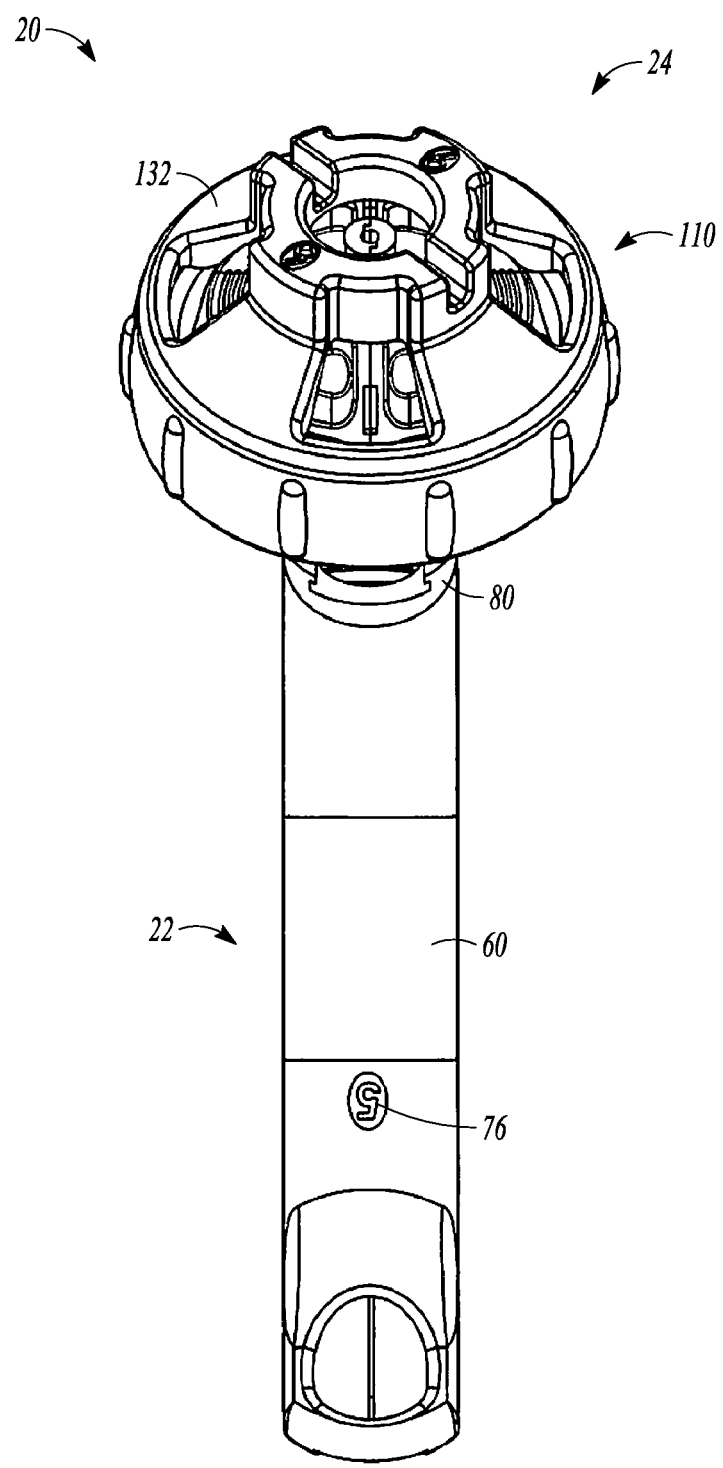
FIG. 9B: illustrates a medial view of the spacer mold of FIG. 9A.
Figure 9C:
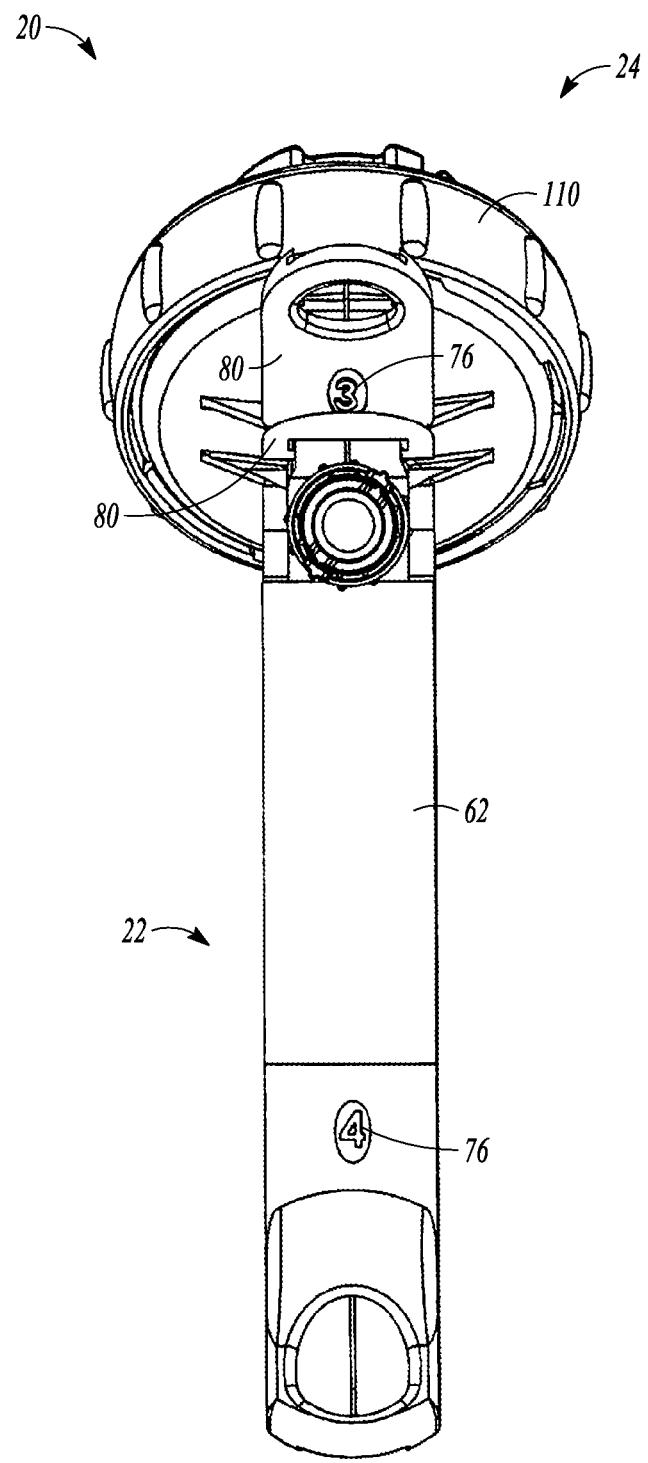
FIG. 9C: illustrates a lateral elevation view of the spacer mold of FIG. 9A.
Figure 9D:
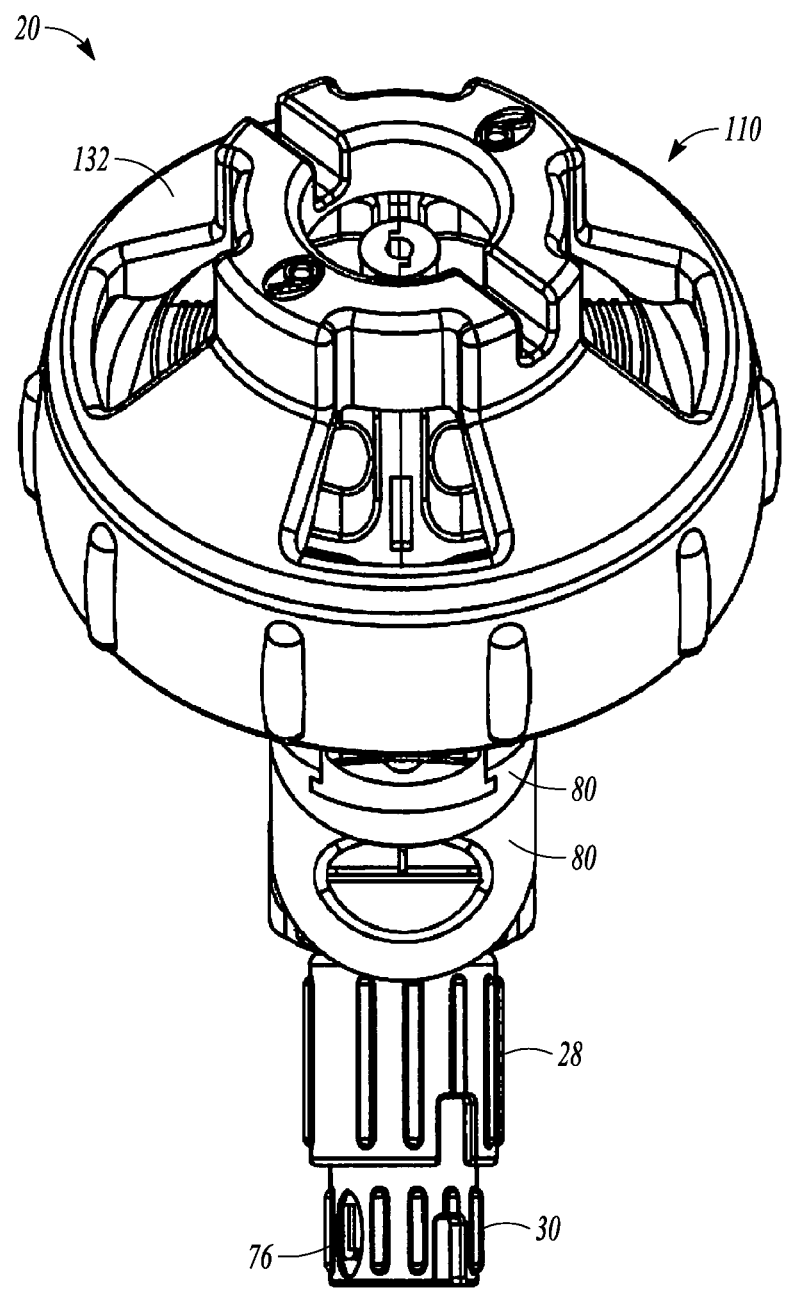
FIG. 9D: illustrates a proximal elevation view of the spacer mold of FIG. 9A.
Figure 9E:
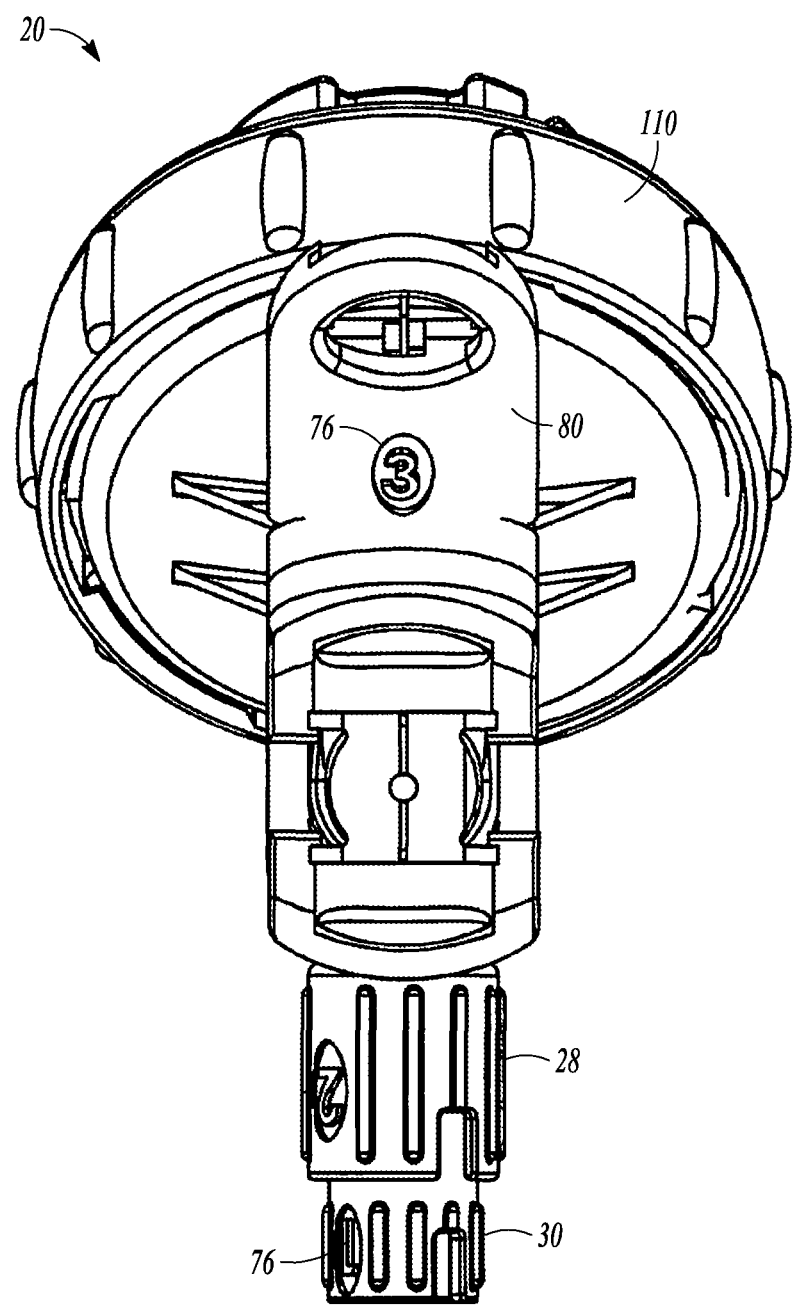
FIG. 9E: illustrates a distal elevation view of the spacer mold of FIG. 9A.
Figure 20:
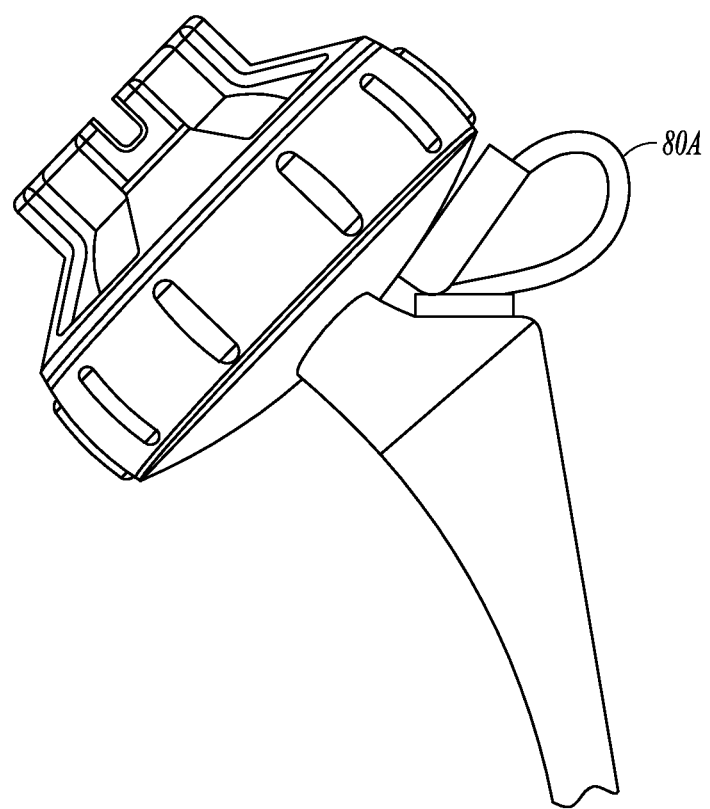
FIG. 20: illustrates an embodiment of a securement member.

Thereafter, a plurality of head chamber securement members 80 are secured to first and second stem members 32 and 34 adjacent head molding chamber walls 82 in a similar manner as described above with respect to first and second stem securement members 60, 62 as shown in FIGS. 1 and 2, with head chamber securement members 80 also including locking lips 73 and undercuts for slidably engaging rails 75, 79 of head molding chamber walls 82 and port portion rails 77 of respective first and second stem members 32, 34. In securing the lower portion of head molding chamber 90, a first head securement member 80 can be slid onto port portion rails 77 of first and second stem members 32, 34. Next, a second head securement member 80 can be slid onto rails 75 of head molding chamber walls 82 of respective first and second stem members 32, 34. Finally, a third head chamber securement member 80 can be slid onto rails 79 of head molding chamber walls 82 of respective first and second stem members 32, 34. It will be appreciated that the foregoing order of placing the head chamber securement members 80 is not important, and that any one of the plurality of head chamber securement members can be placed before or after placement of any other head chamber securement member. In another embodiment, as shown in FIGS. 5, 9A and 20, head chamber securement member 80 is made of a flexible material such that a first end of a head chamber securement member 80a (FIG. 5, feature 80A) can be used to secure rails 79 of head molding chamber wall 82, and an opposing second end of head chamber securement member 80a can be used to secure port portion rail 77 of respective first and second stem members 32, 34.

The stem member securement assembly, including first and second stem securement members 60, 62 and plurality of head chamber securement members 80, restricts separation of stem members 32, 34. For example, the securement member assembly restricts separation of stem members 32, 34 while the cement from a cement gun is injected into space mold 20 under relatively high pressure, such as, for example, at approximately 300 psi to 350 psi.

Figure 10C:
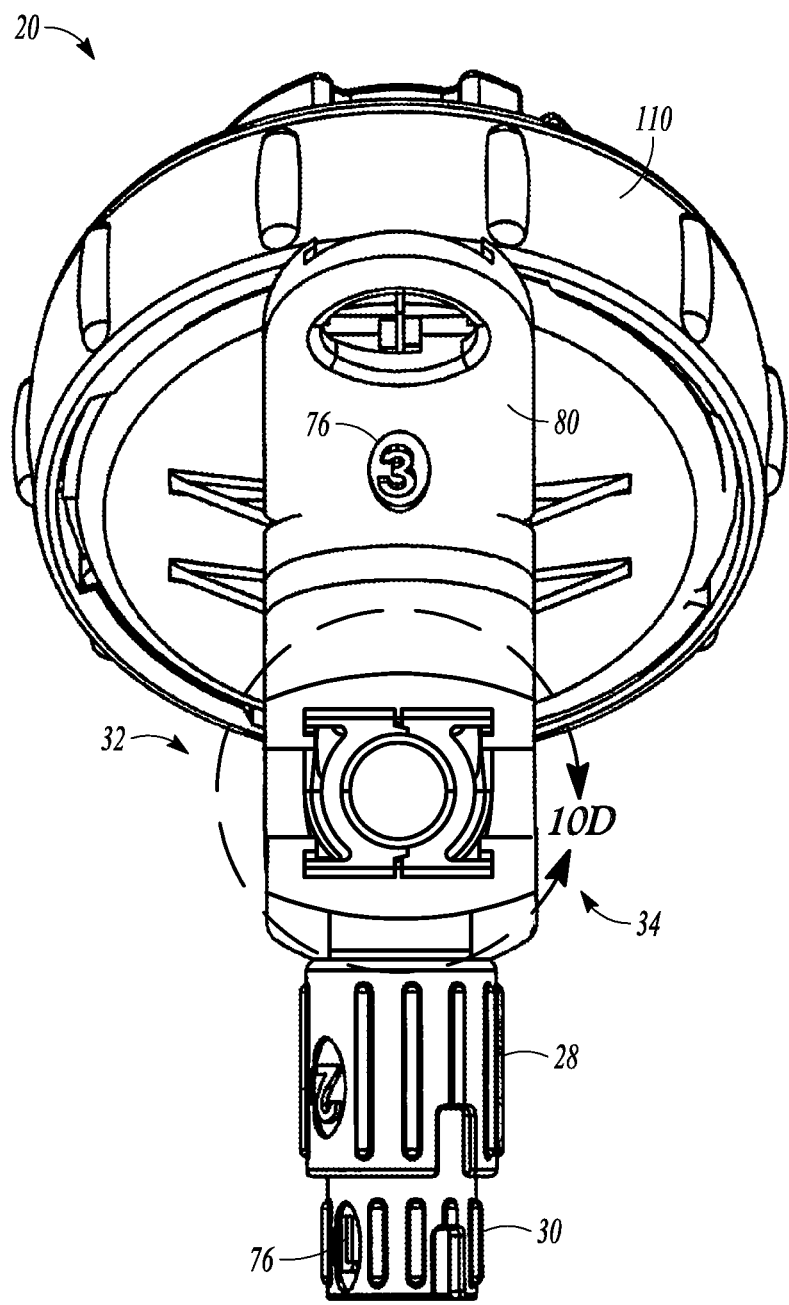
FIG. 10C: illustrates a distal elevation view of the spacer mold of FIG. 10A.
Figure 10D:
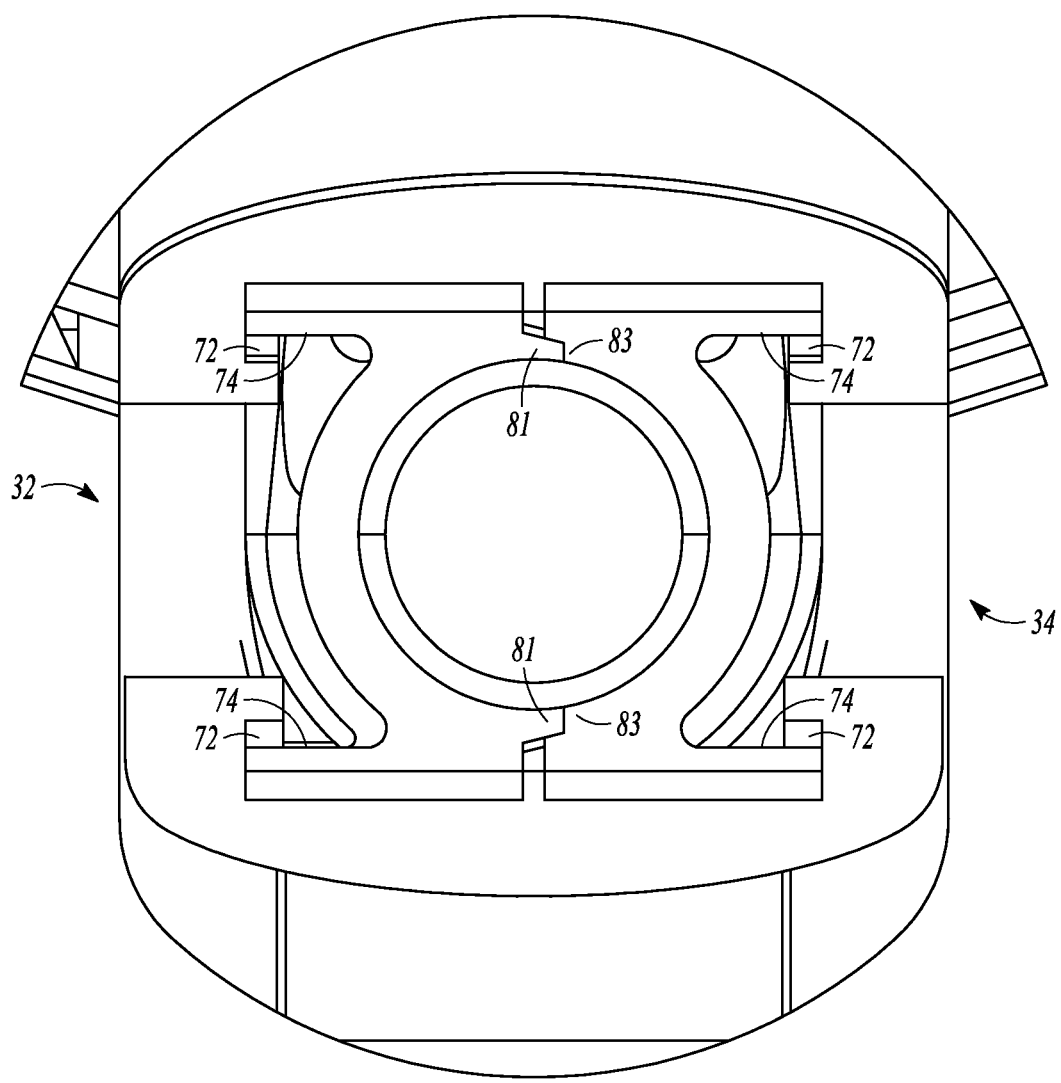
FIG. 10D: illustrates a detailed, fragmentary view of a portion of FIG. 10C.

Referring to FIGS. 10C and 10D, the engaging walls of first and second stem members 32, 34 can include cooperating seal portions, such as deformable lip seal projections 81 which engage and deform against lip seal abutments 83 to form a tight seal along the engaging walls of first and second stem members 32, 34. Although projections 81 are shown on stem member 32 and abutments 83 are shown on stem member 34 in FIG. 10D, projections 81 and abutments 83 can be selectively and cooperatively configured on either or both of stem members 32 and 34.

Figure 16:
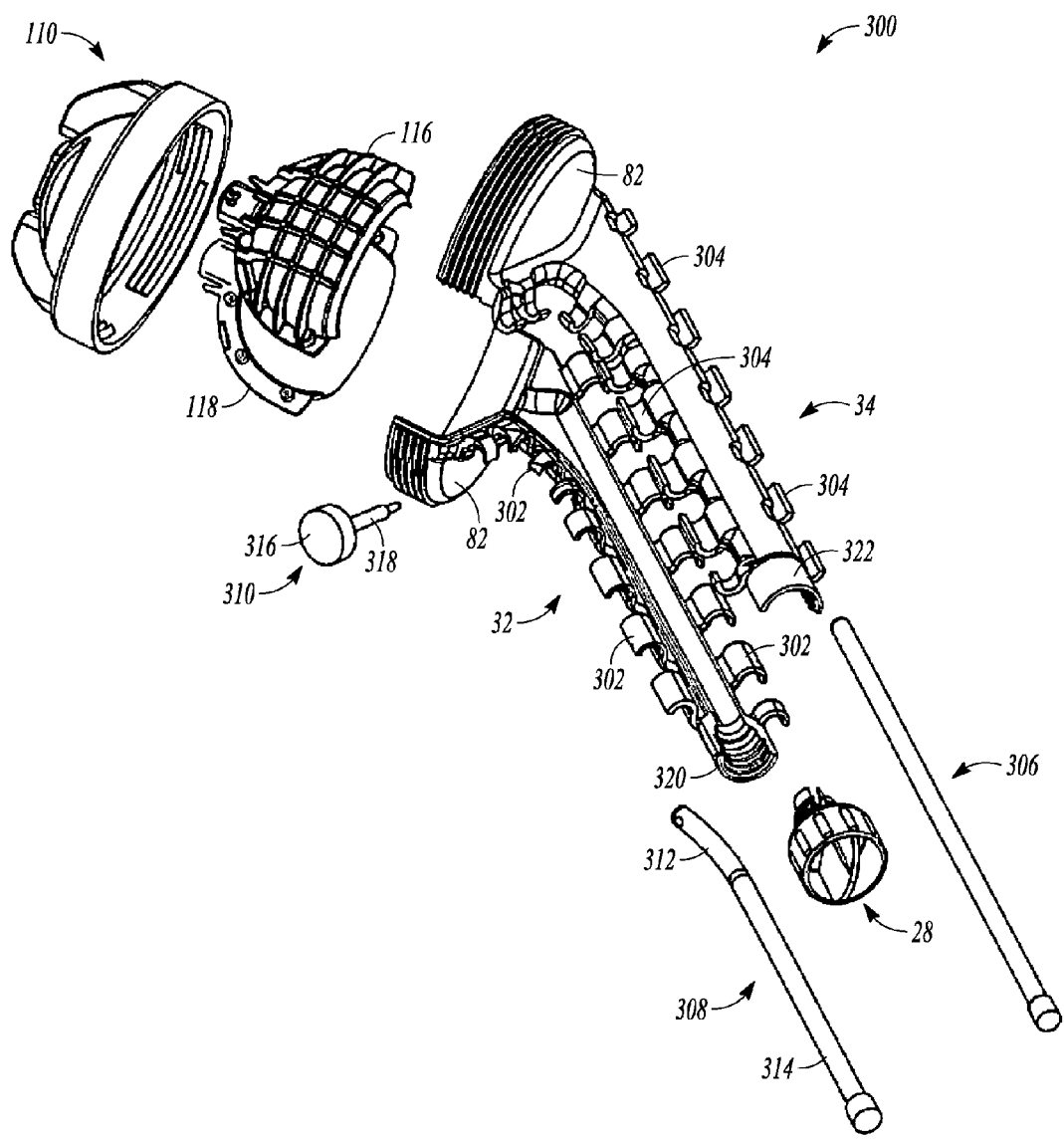
FIG. 16: illustrates an exploded view of a hip spacer mold having a securement assembly according to a further embodiment.
Figure 17:
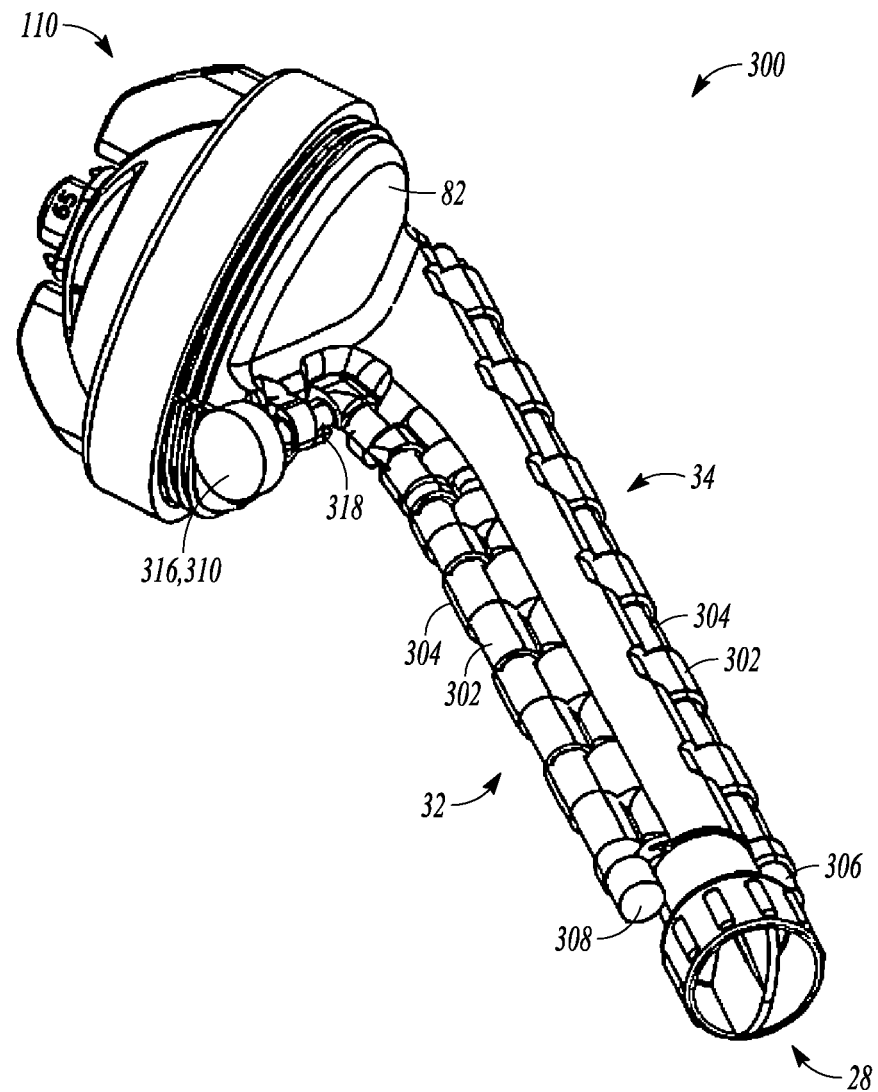
FIG. 17: illustrates an assembled view of the hip spacer mold of FIG. 16.

Referring to FIGS. 16 and 17, expect as described below, a spacer mold assembly 300 is shown having a securement assembly according to another embodiment, but which is otherwise similar to spacer mold 20 described above. First and second stem members 32, 34 each include a series of spaced, substantially half-cylindrical hinge members 302, 304, respectively, extending along the lateral and medial aspects of first and second stem members 32, 34, which, when the first and second stem members 32, 34 are fitted with one another as shown in FIG. 17, alternate or interleave with one another to define substantially continuous channels along the lateral and medial aspects of first and second stem members 32, 34. Hinge pins 306, 308, and 310 are inserted through the channels defined by hinge members 302 and 304 to secure stem members 32 and 34 together. A first hinge pin 306 is inserted through the channel along the lateral aspect of assembly 300, and can be formed of a rigid metal or plastic material, for example, as such channel is substantially linear. A second hinge pin 308 is inserted through the curved channel along the medial aspect of assembly 300, and can include a distal portion 312 made of a somewhat resilient material to conform to the curved portion of the medial channel, and a proximal portion 314 made of relatively rigid material. A third hinge pin 310 can include a head portion 316 and a shaft portion 318 for insertion along a third channel along the medial aspect of assembly 300 beneath the head wall 82. The distal ends 38 of first and second stem members 32, 34 can include respective cooperating port sections 320, 322 adapted to receive a port adapter 28 or, with respect to the above-described embodiment, the filler port can be configured along the lateral or medial aspect of the assembly 300.

Figure 18:
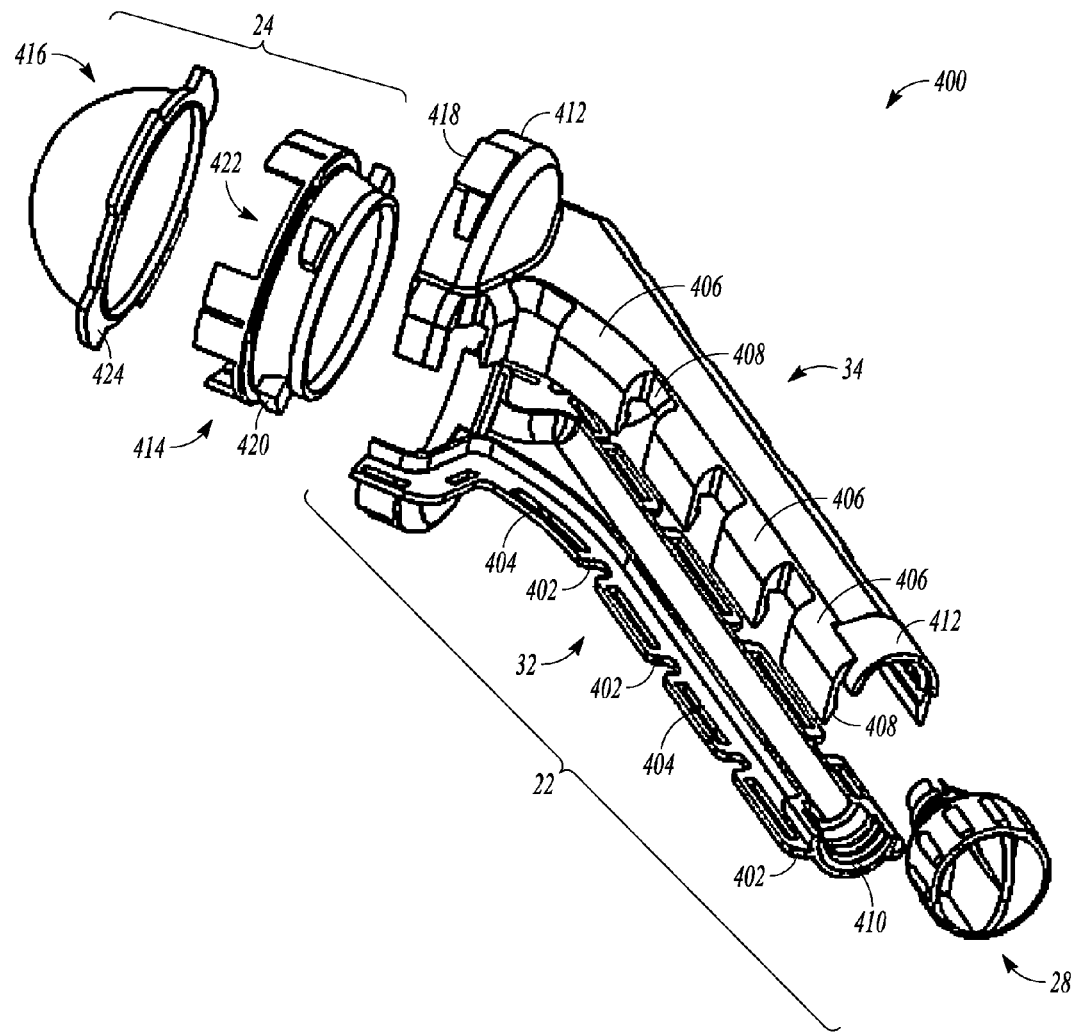
FIG. 18: illustrates an exploded view of a hip spacer mold having a securement structure according to a still further embodiment.
Figure 19:
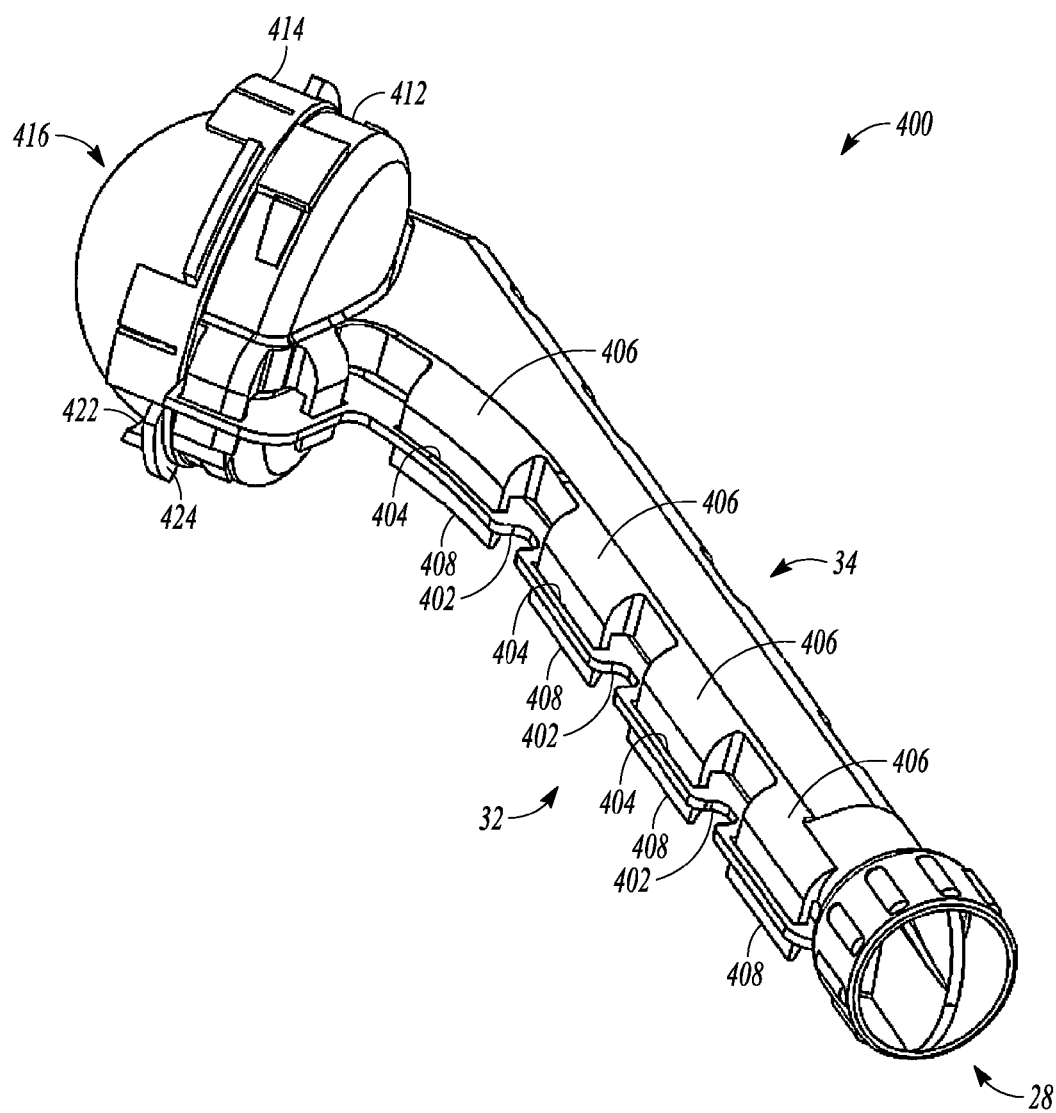
FIG. 19: illustrates an assembled view of the hip spacer mold of FIG. 18.

Referring to FIGS. 18 and 19a spacer mold assembly 400 is shown having a securement assembly according to another embodiment, but which is otherwise similar to spacer mold 20 described above. Stem member 32 includes a series of spaced receptacles 402 with apertures 404 along its lateral and medial aspects, while stem member 34 includes a series of spaced projections 406 with teeth 408 along its lateral and medial aspects. When stem members 32 and 34 are attached to one another, teeth 408 of projections 406 are received within apertures 404 of receptacles 402 to firmly secure stem members 32 and 34 together in a snap-fit, interference fit, locking taper or similar arrangement. Similar to the embodiment of FIGS. 16 and 17, the distal ends of stem members 32 and 34 can include cooperating port sections 410 and 412 adapted to receive a port adapter 28 or, with respect to the above-described embodiment, the filler port can be configured along the lateral or medial aspect of the assembly 400. The spacer mold assembly can include a head portion 401 configured to be removably attachable to the stem portion 22, the head portion 401 including a head adapter 414 and a head member 416. The head member 416 can have a concave, arcuate interior surface that defines the upper portion of head molding chamber 90 to mold at least a portion of a rounded or spherical outer surface at proximal end 210 of spacer head 202 (FIG. 12). A head molding chamber portion 412 of the first and second stem members 32, 34 can include a series of radially spaced apertures 418, and the head adapter 414 can include a series of radially spaced projections 420 configured to be received within the spaced apertures 418 of head chamber portion 412 to secure the head adapter 414 to the head chamber portion 412. In an alternate embodiment, the head molding chamber portion 412 can have a series of radially spaced projections 420 and the head adapter 414 can have a series of radially spaced apertures 418 configured to receive the radially spaced projections 420 of the head molding chamber portion 412. Head adapter 414 can include a series of radially spaced notches 422, and the head member 416 can include series of radially spaced flanges 424 configured to be received within the notches 422 of head adapter 414 to secure the head member 416 to head adapter 414. In an alternate embodiment, head adapter 414 can have a series of radially spaced flanges 424 and head member 416 can have a series of radially spaced notches configured to receive the flanges 424 to secure head member 416 to head adapter 414. The spaced projections and flanges 420, 424 can form a locking, snap-fit, an interference fit or other similar arrangement with the spaced apertures and notches 418, 422 to secure the head adapter 414 to head molding chamber 412 of first and second stem members 32, 34 and to secure head member 416 to head adapter 414.

To properly match the actual size of a particular hip joint implant site for a patient, stem portion 22 of spacer mold 20 can be provided in a variety of different sizes. In one embodiment, first and second stem members 32, 34 are available in a variety of different lengths. In this manner, the size of the stem cavity 40 can be varied, for example, the stem cavity length can be varied. In another embodiment, first and second stem members 32, 34 can be ordered from a manufacturer after an implant site of a patient is conveniently measured with x-rays, imaging, or other non-invasive scanning technology. In other embodiments, for example, a plurality of stem portions 22 can be provided in a kit so that a surgeon can use the closest fitting stem portion during a surgical procedure when the implant site is open and accessible for measurement. While a set of stem portions 22 can have cavities 40 of varying sizes, each stem portion 22 will have the same or similar exterior dimensions for attachment to a single securement assembly 60, 62, 80 and only the interior dimensions of the alternative stem portions 22 change to correspond to different cavity 40 sizes.

Figure 7:
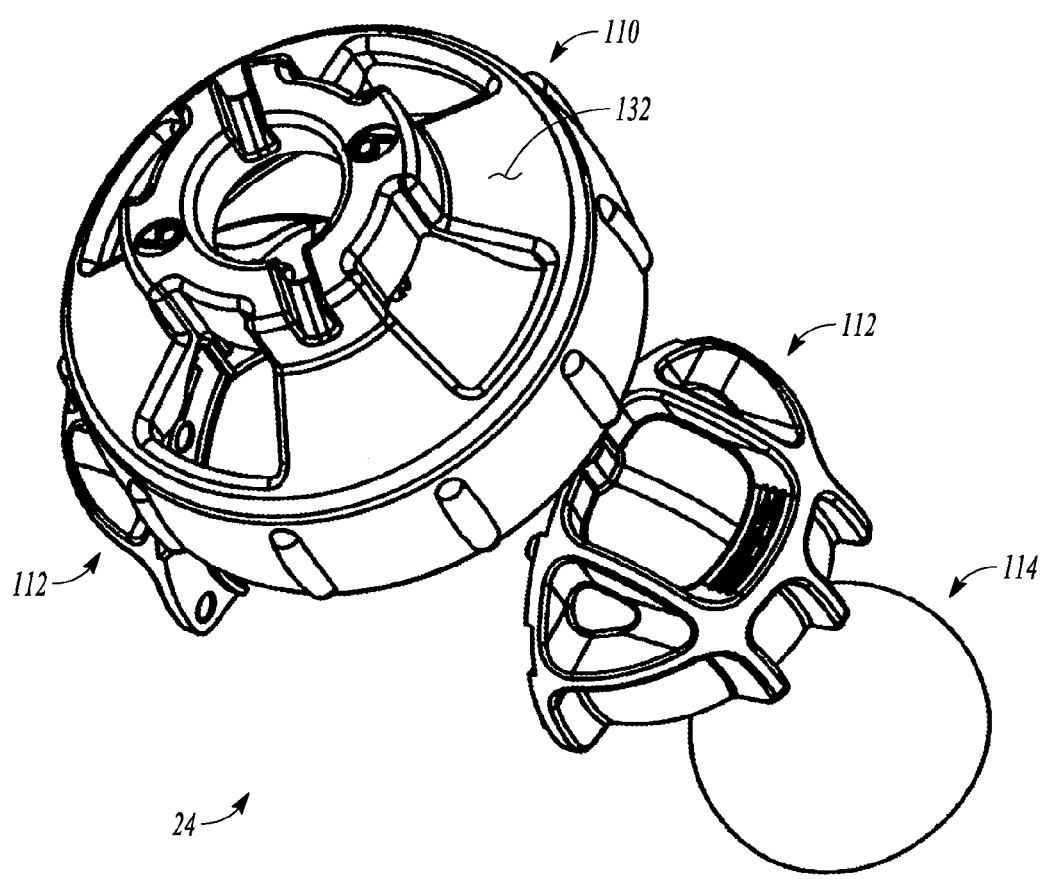
FIG. 7: illustrates an exploded view of a head mold assembly of the spacer mold of FIG. 1.

Referring to FIG. 5, a surgeon can obtain stem portion 22 of spacer mold 20 for a surgical procedure preassembled as described above. In this manner, all components of spacer mold 20 are preassembled for the surgeon except for the head portion 24 and optionally port adapter 28 and plug 30. As previously discussed, preassembled stem portions 22 of spacer mold 20 can be available in a kit containing a variety of different sized stem portions 22 so that a surgeon can select an appropriate size spacer mold 20 for a particular patient. Once an appropriately sized stem portion 22 is selected, a surgeon next selects an appropriately sized head portion 24 (FIG. 7). To add even further adaptability and to properly match the actual size of a particular hip joint implant site for a patient, head portion 24, which includes head securing member or bell housing 110, head module 112, and head adapter 114, is also provided in a variety of different sizes and are interchangeable on stem portion 22.

Referring to FIGS. 6 and 7, the method of assembling bar adapter 114, head module 112, and head securing member 110 to stem portion 22 of spacer mold 20 by a user such as a surgeon during surgery will now be described. Referring to FIG. 6, a surgeon selects a particularly sized bar adapter 114 and secures bar adapter 114 to head 52 of reinforcing bar 50 by threadingly connecting an internal threaded portion 115 (FIGS. 10B and 10E) of bar adapter 114 with external threaded portion 53 of reinforcing bar 50 (FIGS. 8A-8D). Bar adapter 114 can also be attachable to head 52 of reinforcing bar 50 by other connection configurations such as mating protrusion and locking aperture, snap-fit or similar connection mechanism. In one embodiment, bar adapter 114 is made out of bone cement, for example, PMMA. In such an embodiment, bar adapter 114 is formed before injecting spacer mold 20 with bone cement, and is provided in a variety of different sizes. By having a pre-formed bar adapter 114 that is secured to head 52 of reinforcing bar 50, the amount of bone cement needed to be injected in spacer mold 20 is reduced by the volume of bar adapter 114.

Once bar adapter 114 is secured to head 52 of reinforcing bar 50, a surgeon selects a particularly sized head module 112. In one embodiment, head module 112 includes first and second head module members 116, 118 (FIG. 11) together defining an appropriately sized inner diameter $D_2$ (FIG. 6). Referring to FIGS. 6, 7, and 11, in one embodiment, head module 112 includes first and second head module members 116, 118 that are mirror images of each other (one head module member 116 of head module 112 is shown in FIGS. 6 and 7). Referring to FIG. 11, first and second head module members 116, 118, each have a concave, arcuate, interior surface 120, 122, respectively, that are contiguous with each other to cooperatively form a generally continuous molding surface to form the upper portion of head molding chamber 90. Referring to FIG. 11, interior surfaces 120, 122 of respective first and second head module members 116, 118 mold at least a portion of a rounded or spherical outer surface 210 of spacer head 202 (FIG. 12). In one embodiment, interior surfaces 120, 122 provide outer surface 210 of spacer head 202 with a shape that is generally about ¾ of a sphere or otherwise matches an articular surface of a bone, such as a femur. Interior surfaces 120, 122 respectively terminate at a lower, arcuate surface or end 124, 126 of respective first and second head module members 116, 118 and are configured to seat on the bottom 86 of the lower portion 90 of head molding chamber 90 as will be further discussed below.

In one embodiment, head module 112 can be provided in a variety of different sizes. For example, head module members 116, 118 can be available having inner diameters $D_2$ (FIG. 6) of approximately 50 mm, 53 mm, 56 mm, 59 mm, 62 mm, or 65 mm, for example. When such a set is provided during a surgical procedure, the surgeon can measure the diameter of the acetabulum, or the remaining void on the hip when an implanted acetabular cup is removed from the hip to clear the infection, and then select a head module 112 or head module members 116, 118 with the closest matching inner diameter $D_2$. While a set of head modules 112 can have inner diameter of $D_2$ of varying sizes, each head module 112 will have the same or similar exterior dimensions so that they all fit on any sized stem portion 22 to provide maximum adaptability. In other embodiments, other configurations are contemplated where only certain head module 112 sizes can be used with stem portions of a certain size.

Referring to FIGS. 6, 10B, and 11, in one embodiment head module 112, including first and second head module members 116, 118 are received within proximal end 36 of stem portion 22 and cooperate to define the upper portion of head molding chamber 90. With head module 112 properly positioned within head molding chamber 90, head securing member 110 removably attaches to first and second stem members 32, 34 to hold first and second head module members 116, 118 adjacent to bottom 86 of head molding chamber 90. Head securing member 110 keeps first and second head module members 116, 118 adjacent to bottom 86 of head molding chamber 90, i.e., in generally fixed relation to bottom 86 of head molding chamber 90 while receiving pressurized cement during filling of spacer mold 20 and setting of the cement within the head molding chamber 90.

Referring to FIGS. 6, 7 and 10B, head securing member 110 includes cover portion 132 and an internally threaded portion 134 (FIGS. 10B and 10E) that threadingly engages external threaded portion 94 of head molding chamber cylindrical walls 88 of stem members 32, 34. In such a configuration, head securing members 110 can be threaded on and unthreaded from head molding chamber cylindrical walls 88 of stem members 32, 34 to releasably hold head module 112 (including first and second head module members 116, 118) to bottom 86 of head molding chamber 90 to form spacer head 202 of hip spacer 200 therein. Referring to FIG. 11, in one embodiment first and second head module members 116, 118 have opposing surfaces with pegs 140 on one head module member 116 that fit holes 142 on the other head module member 118. In an alternate embodiment, head module member 118 has pegs 140 that fit opposing holes 142 of head module member 116. With head securing member 110 holding head module members 116, 118 to bottom 86 of head molding chamber 90 as described above, head securing member 110 pulls the opposing surfaces of head module members 116, 118 against each other and maintains pegs 140 in respective holes 142.

Figure 13:
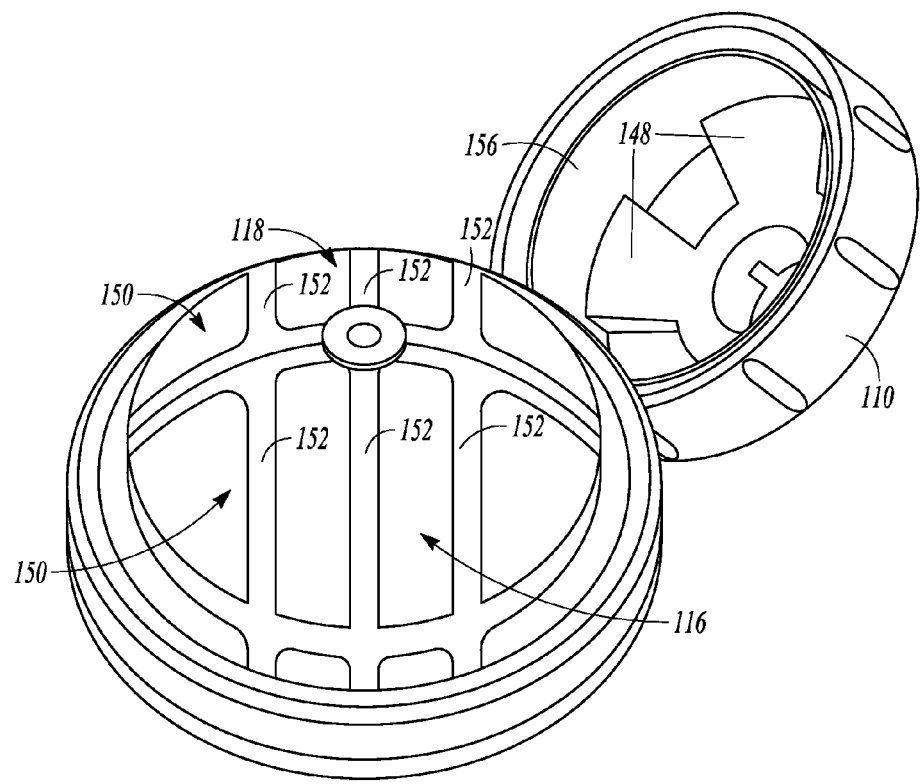
FIG. 13: illustrates an exploded view of the spacer mold of FIG. 1 with a head securing member of the spacer mold removed.

Referring to FIG. 13, in one embodiment, head securing member 110 includes protrusions 148 that project interiorly into the interior of head securing member 110. Protrusions 148 can engage grooves 150 defined by flanges 152 that form the exterior of head module members 116, 118. With protrusions 148 seated within grooves 150 on flanges 152, head module members 116, 118 will rotate with head securing member 110 when head securing member 110 is being removed from stem portion 22 after curing spacer 200. This facilitates breaking bonds between dried cement of head portion 202 of spacer 200 and the interior surfaces 120 and 122 (FIG. 11) of head module members 116, 118. Once head securing member 110 is removed, head module 112 and head module members 116, 118 can be pulled off head portion 202 of spacer 200.

Figure 10E:
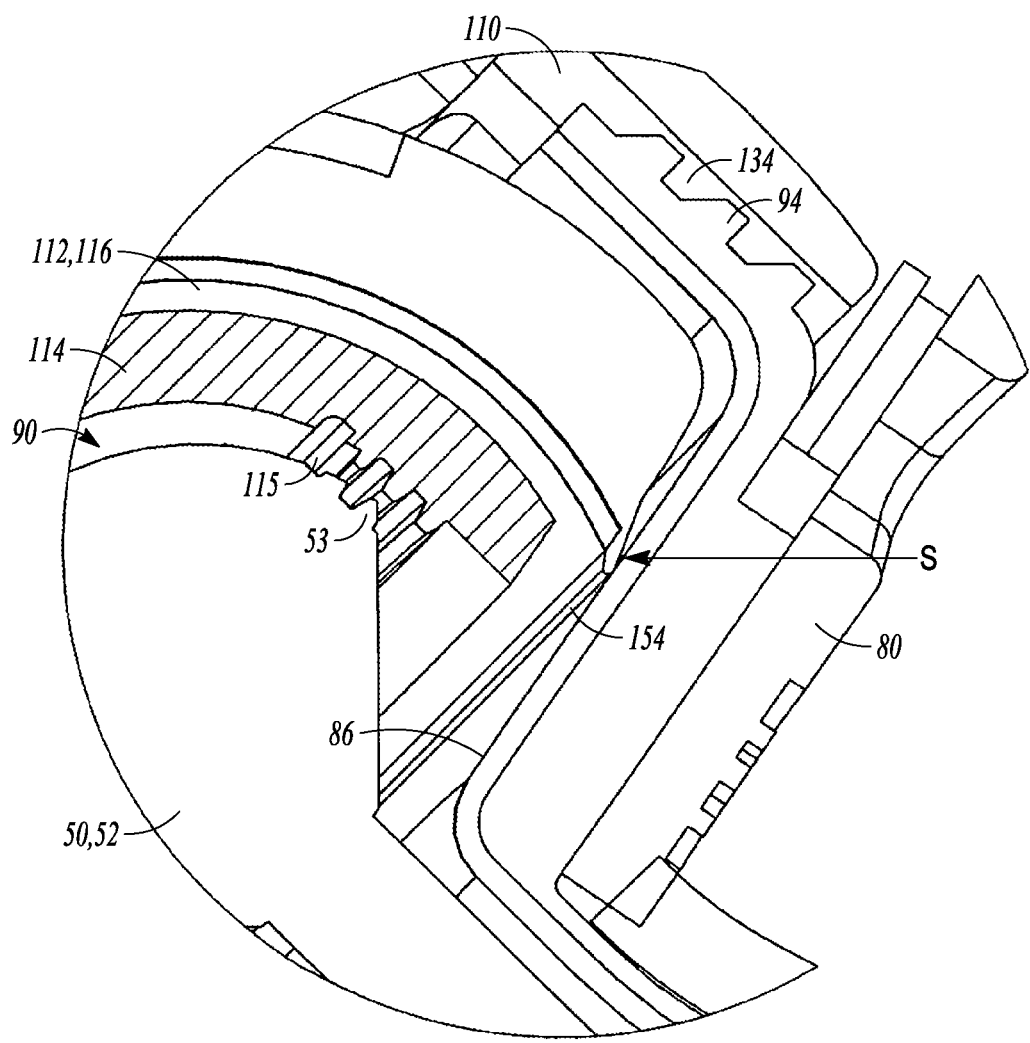
FIG. 10E: illustrates a detailed, fragmentary view of a portion of FIG. 10B.

Referring to FIG. 10E, the orientation of head module 112 and head module members 116, 118 (FIG. 11) relative to bottom 86 of head molding chamber 90 will now be described. Referring to FIGS. 6 and 10E, head module 112 and head module members 116, 118 each include sealing lip 154 disposed at a bottom portion of a respective head module member. Referring to FIG. 10E, with head module 112 and head module members 116, 118 properly positioned within head molding chamber 90, and with head securing member 110 threadingly connected to first and second stem members 32, 34 as described above, flexible sealing lip 154 abuts a portion of bottom 86 of head molding chamber 90 at sealing point S (FIG. 10E). In this manner, cement is prevented from seeping outwardly beyond sealing point S between sealing lip 154 and bottom 86 of head molding chamber 90.

Figure 14:
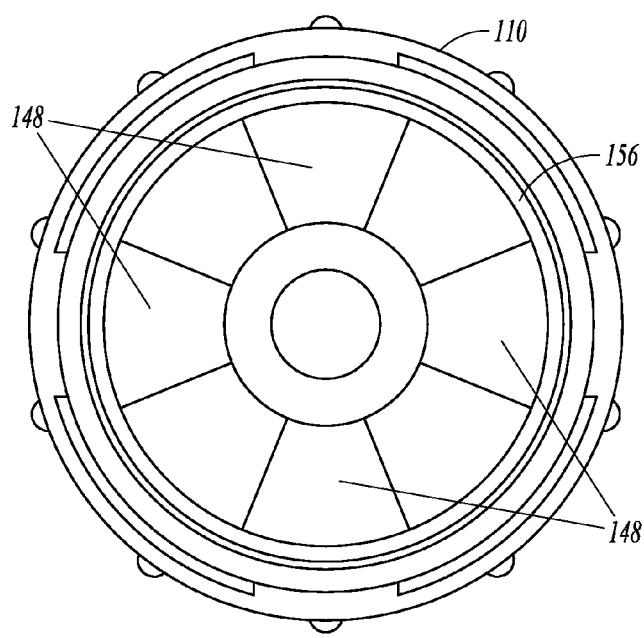
FIG. 14: illustrates a bottom perspective view of the head securing member of FIG. 13.

Referring to FIGS. 11, 13 and 14, in one embodiment, head securing member 110 includes sealing ring 156. In one embodiment, sealing ring 156 is a separate component from head securing member 110 that can be removably attached to an interior portion of head securing member 110 as shown in FIG. 13. With sealing ring 156 secured within head securing member 110 as shown in FIG. 13, head securing member 110 is threadingly connected to first and second stem members 32, 34 as described above and, in such a manner, sealing ring 156 is secured around a periphery of head module 112 and head module members 116, 118 to prevent head securing member 110 from separating from head module 112 and head module members 116, 118 during the molding process due to the pressure build-up during the filling of the spacer mold 20 and setting of the cement within head molding chamber 90. In this manner, cement is prevented from seeping out of head module 112 and head module members 116, 118 during the filing of the spacer mold 20 and setting of the cement within head molding chamber 90. In other embodiments, sealing ring 156 is an integral component with the interior of head securing member 110. Sealing ring 156 is secured to a periphery of head module members 116, 118 using an interference connection to provide a secure fit therebetween. In other embodiments, sealing ring 156 can be secured to a periphery of head module members 116, 118 by means of complimentary locking tapers or other similar securement means.

Referring to FIGS. 1 and 2, a use of spacer mold 20 to create a spacer (e.g., a hip spacer) to be used as a temporary implant or spacer made of a antibiotic-filled cement will now be described. With spacer mold 20 completely assembled, the nozzle of the cement gun can be directly threaded onto threads 160 (FIG. 2) of port 100. If necessary, a port adapter 28 is selected, which includes interior threaded portion 162 (FIG. 10B) which can be removably attached to port 100 by threadingly connecting threaded portion 162 of port adapter 28 to threads 160 of port 100 as shown in FIG. 10B. With port adapter 28 secured to port 100, the nozzle of a second cement gun can be threadingly connected to port adapter 28 via second interior threaded portion 164 (FIG. 10B) of adapter 28.

With the nozzle of the cement gun secured to port 100 or port adapter 28, a surgeon can inject cement such as high-strength, high viscosity PMMA from a cartridge of a cement gun to inject the cement into spacer mold 20 to form hip spacer 200. Once spacer mold 20 is sufficiently filled with cement, the nozzle of the cement gun is removed from port adapter 28 or port 100, and plug 30 can be secured to port 100 or port adapter 28 as shown in FIG. 10B.

Figure 15:
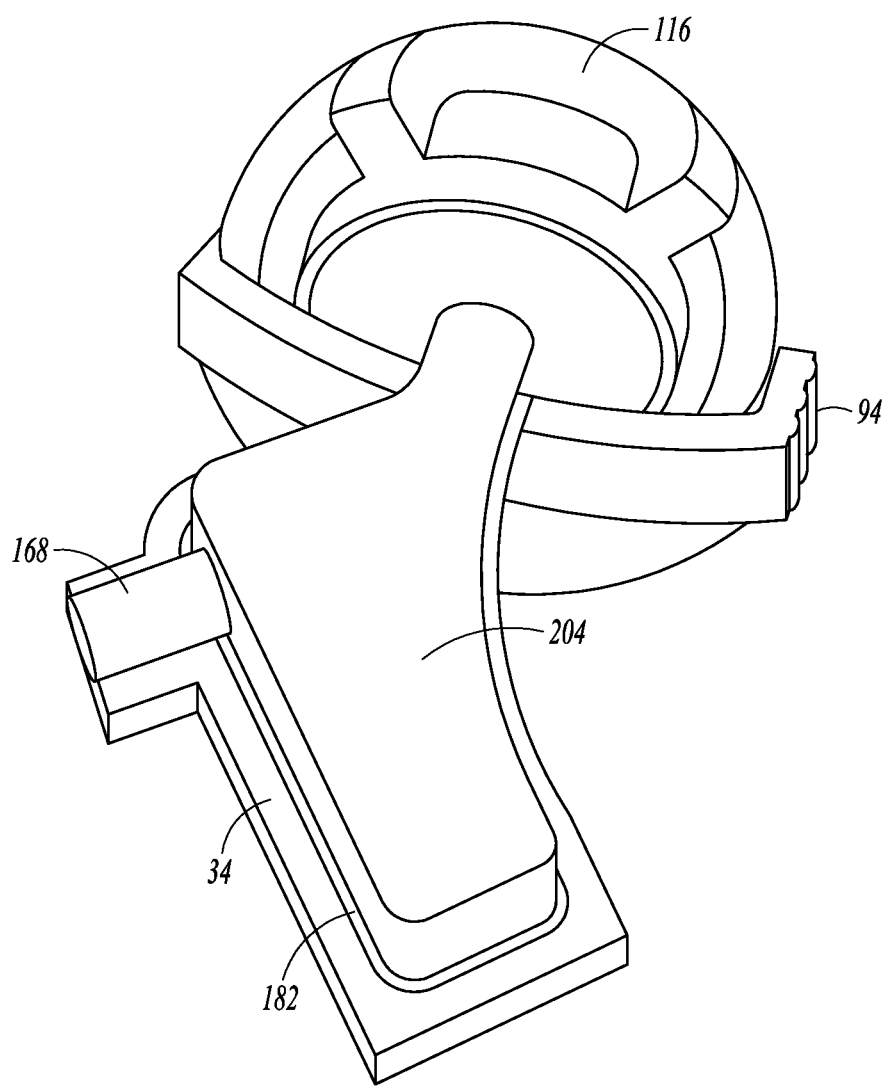
FIG. 15: illustrates a perspective view of a partial hip spacer disposed within a partial spacer mold in accordance with the present disclosure.

Referring to FIGS. 2, 4, 10B and 15, the use of plug 30 to prevent flash 168 in the channel of port 100 will now be described. After the cement gun is used to inject cement into spacer mold 20, and the nozzle of the cement gun is removed from port 100 or port adapter 28, excess cement in spacer mold 20 will seep into the channel of port 100 and, if allowed to cure, would form flash 168 (FIG. 15). To prevent flash 168 from being formed in the channel of port 100, plug 30 is used which, as shown in FIG. 4, includes plug head 170, threaded portion 172, flash preventing post 174, and slots 176 (FIG. 2) disposed at plug head 170. After the nozzle of the cement gun is removed from port 100 or port adapter 28, flash preventing post 174 is inserted within the channel of port 100 and plug is threadingly connected to port adapter 28 via threaded portion 172 of plug 30 and second interior threaded portion 164 of port adapter 28 as shown in FIG. 10B. In other embodiments, plug 30 can be threadingly connected to threads 160 (FIG. 2) of port 100 via threaded portion 172 of plug 30. In this manner, flash preventing post 174 forms a physical barrier in the channel of port 100 and prevents the formation of flash 168 (FIG. 15).

Referring to FIG. 2, plug 30 includes slots 176 and port adapter 28 includes slots 194. Slots 176 and 194 can be used to receive a tool for tightening and loosening port adapter 28 to port 100 and plug 30 to port adapter 28 or port 100.

Referring to FIGS. 10B and 15, stem members 32, 34 each include a peripheral groove 182 that extends around the periphery of stem members 32, 34 (FIG. 15 illustrates trialing spacer mold having a shorter stem member). Peripheral grooves 182 prevent cement seepage from the interior cavity of spacer mold 20 during injection of cement and hardening of the cement.

Referring to FIG. 10B, spacer mold 20 is not permanently sealed and spacer mold 20 includes head portion vent 184 and distal end vent 186. Vents 184, 186 permit gas or air to exhaust from spacer mold 20 as the spacer mold is being filled with cement. Vents 184, 186 also can provide visual indication that spacer mold is filled with cement when cement begins to flow out of either vent 184, 186.

In one embodiment, further ventilation of gas or air from spacer mold 20 can be provided by having the inner diameter of head securing member 110 slightly larger than the widest external dimension of first and second head module members 116, 118 so that a slight opening or space exists between head module members 116, 118. In such an embodiment, the slight opening or space communicates with head portion vent 184 to permit gas or air to exhaust from head molding chamber 90 and escape spacer mold 20.

Figure 3:
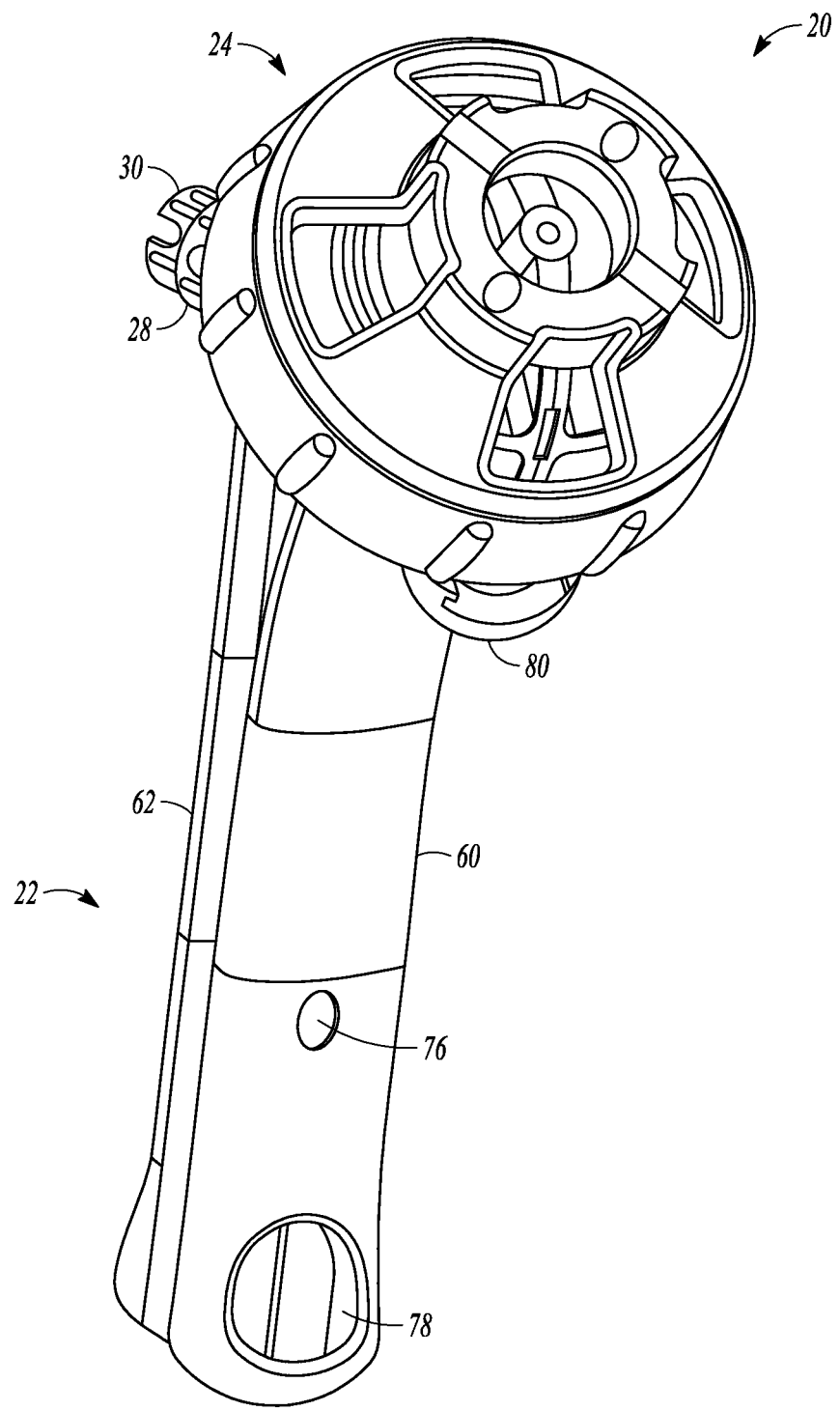
FIG. 3: illustrates a perspective view of the spacer mold of FIG. 1.

With plug 30 secured to port 100 or port adapter 28 as discussed above, the spacer mold 20 can be placed on a surface to let the cement cure. Once the cement is hardened and has cured, spacer mold 20 can be disassembled to remove hip spacer 200 from inside spacer mold 20 in the following manner. In one embodiment, the components of spacer mold 20 are numbered to describe the order of disassembly of spacer mold 20 to remove hip spacer 200 from spacer mold 20. For example, indicia 76 can be disposed on first and second securement members 60 and 62, the plurality of head chamber securement members 80, port adapter 28 and plug 30 as shown in FIGS. 1-6. In such an embodiment, referring to FIGS. 1-6, plug 30 would be disassembled from spacer mold 20 first and, thus, plug 30 is labeled with the number one (FIG. 2). Next, port adapter 28 is removed, and thus, port adapter 28 is labeled with the number two (FIG. 2). Next, head chamber securement members 80 would be disassembled from spacer mold 20 and, thus, head chamber securement members 80 are labeled with the number three (FIGS. 1 and 2). Subsequently, second stem securement member 62 is removed and, thus, is labeled with the number four (FIG. 1). Next, first stem securement member 60 is removed and, thus, is labeled with the number five (FIG. 3). Next, head securing member 110 can be unthreaded from first and second stem members 32, 34 and stem members 32, 34 pulled apart. At this point, spacer mold 20 will look similar to that illustrated in FIG. 15. Next, referring to FIGS. 13 and 15, a surgeon can grasp modular head members 116, 118 and pull modular head members 116, 118 and hip spacer 200 from stem members 32, 34. Next, a surgeon can pull first modular head member 116 from second modular head member 118. Finally, the last head module member 118 can be removed from hip spacer 200 thereby freeing hip spacer 200 completely from spacer mold 20. At this point, any remaining flash can be knocked off. Once hip spacer 200 is removed from spacer mold 20, spacer mold can be disposed of. Disposable spacer mold technologies prevent medical practitioners from being burdened with the cleaning and sterilization procedures required to reuse surgical instruments, which can be expensive and time consuming. While this disclosure has been described as having exemplary designs, the present disclosure can be further modified within the spirit and scope of this disclosure.

The above Detailed Description includes references to the accompanying drawings, which form a part of the Detailed Description. The drawings show, by way of illustration, specific embodiments in which a handle assembly and related methods can be practiced. These embodiments are also referred to herein as "examples." While certain examples are shown and described with respect to a left or a right handle orientation, it is to be appreciated that the present disclosure is equally applicable to both left and right handles.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient. In this document, the phrase "anterior/posterior direction" is used to include an anterior to posterior direction or a posterior to anterior direction.

In the appended claims, the terms "having," "including" and "in which" are used as the plain-English equivalents of the respective terms "comprising" and "wherein." The terms "having", "including" and "comprising" are open-ended, that is, an apparatus, system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A prosthetic mold, comprising:
    a stem portion defining a cavity having a shape of a femoral stem, the stem portion including a first stem member having a first engagement member, and a second stem member having a second engagement member, each one of the first and second engagement members projecting from a wall of the respective first and second stem members; and
    a C-shaped securement member, separable from the stem portion, the securement member configured to slide along a length of the first engagement member and a length of the second engagement member to secure the first and second stem members to each other.

2. The prosthetic mold of claim 1, wherein each one the first and second engagement members comprises a medial flange and a lateral flange, the securement member comprising a medial member and a lateral member, the medial member configured to slidably engage the medial flange of each of the first and second engagement members and the lateral member configured to slidably engage the lateral flange of each of the first and second engagement members.

3. The prosthetic mold of claim 1, wherein each of the first and second engagement members comprises a track, and wherein the securement member comprises a rail.

4. The prosthetic mold of claim 1, wherein each of the first and second engagement members comprises a rail and the securement member comprises a track.

5. The prosthetic mold of claim 1, wherein the securement member includes a locking lip and an undercut.

6. The prosthetic mold of claim 1, wherein the first and second engagement members each define a substantially continuous rail configured to engage, respectively, a first track and a second track of the securement member.

7. The prosthetic mold of claim 1, wherein the securement member comprises a track configured to slidably receive the first and second engagement members substantially along the length of the first and second stem members.

8. The prosthetic mold of claim 1, where the first and second stem members each further comprise a head chamber portion configured to form a lower portion of a head cavity.

9. The prosthetic mold of claim 8, wherein a first head chamber portion and a second head chamber portion each comprise a plurality of head chamber engagement portions configured to slidably engage a corresponding plurality of the securement members.

10. The prosthetic mold of claim 8, further comprising a head portion removably attachable to the head chamber portion.

11. The prosthetic mold of claim 10, wherein the head chamber portion of each of the first and second stem members includes a threaded wall, and wherein the head portion includes a head module, having a concave arcuate interior surface defining an upper portion of the head cavity and disposed between the head securing member and the head chamber portion, and a head securing member, configured to engage the threaded wall to secure the head module to the head chamber portion.

12. The prosthetic mold of claim 11, wherein the head module comprises at least two head module members.

13. The prosthetic mold of claim 1, wherein the stem portion further comprises a port in communication with the stem cavity.

14. The prosthetic mold of claim 1, wherein the first and second stem members each further comprise a cooperating seal portion.

15. The prosthetic mold of claim 14, wherein the cooperating seal portion of the first stem member comprises one of a projection or an abutment, and wherein the cooperating seal portion of the second stem member comprises the other one of a projection or an abutment.

16. The prosthetic mold of claim 1, wherein the first engagement member is disposed in a like position or in mirror image to the second engagement member.

17. A prosthetic mold, comprising:
a stem portion, extending from a proximal end to a distal end, including a first stem member and a second stem member configured to mate to each other to cooperatively define a stem cavity having a shape of a femoral stem, the first stem member having a plurality spaced receptacles projecting outwardly from an external wall of the first stem member, each one of the spaced receptacles defining a spaced aperture, and the second stem member having a plurality of spaced teeth projecting outwardly from an external wall of the second stem member, each one of the spaced apertures configured to slidably receive a corresponding one of the plurality of spaced teeth to secure the first and second stem members to each other.

18. The prosthetic mold of claim 17, wherein the plurality of spaced teeth are formed in a plurality of spaced projections extending from the external wall of the second stem member.

19. The prosthetic mold of claim 18, wherein the plurality of spaced teeth are configured to slidably engage the plurality of spaced apertures in a snap-fit arrangement, an interference fit arrangement, or a locking taper arrangement.

20. The prosthetic mold of claim 17, wherein the first and second stem members each further comprise a head chamber portion, configured to form a lower portion of a head cavity, at the proximal end.

21. The prosthetic mold of claim 20, wherein a first head chamber portion comprises a plurality of spaced apertures, and wherein a second head chamber portion comprises a plurality of spaced projections configured to be received within the plurality of apertures.

22. The prosthetic mold of claim 20, further comprising a head portion removably attachable to the head chamber portion, the head portion including a head adapter and a head member, the head member having an arcuate interior surface and defining an upper portion of the head cavity.

23. The prosthetic mold of claim 22, wherein the head chamber portion of the first and second stem members includes one of spaced projections or spaced apertures, and wherein the head adapter includes the other one of spaced projections or spaced apertures, the spaced apertures configured to receive the spaced projections to secure the head adapter to the head chamber portion.

24. The prosthetic mold of claim 23, wherein the head adapter further comprises a plurality of radially spaced notches, and wherein the head member further comprises a plurality of radially spaced flanges configured to be received within the plurality of notches to secure the head member to the head adapter.

25. The prosthetic mold of claim 24, wherein the spaced projections form a snap-fit or an interference fit with the spaced apertures, and wherein the spaced flanges form a snap-fit or an interference fit with the spaced notches.

26. The prosthetic mold of claim 17, wherein the stem portion further comprises a port, in communication with the stem cavity, disposed at the distal end.

27. The prosthetic mold of claim 17, wherein the first and second stem members each further comprise a cooperating seal portion.

28. The prosthetic mold of claim 27, wherein the cooperating seal portion of the first stem member comprises one of a projection or an abutment, and wherein the cooperating seal portion of the second stem member comprises the other one of a projection or an abutment.

29. A prosthetic mold system, comprising:
a plurality of stem molds each defining a shape of a femoral stem, each one of the plurality of stem molds having a stem portion including a first stem member having a first engagement member, and a second stem member having a second engagement member, the first and second engagement members each comprising one of a planar rail or a track configured to receive a planar rail, each one of the planar track and rail extending continuously along substantially the length of the respective first and second stem members, the first and second stem members configured to engage with one another to define a stem mold exterior and a stem mold interior cavity, wherein the stem mold exterior includes at least one dimension that is substantially the same for each one of the plurality of stem molds, and the interior cavity includes at least one dimension that is different for each one of the plurality of stem molds; and a C-shaped securement member assembly comprising the other one of a rail or a track, the securement member separable from the first and second engagement members and configured to simultaneously engage the first engagement member and the second engagement member of any one of the plurality of stem molds to secure the first and second stem members to each other.

30. The prosthetic mold system of claim 29, wherein the exterior dimension is a stem portion length and the interior dimension is an interior cavity length.

31. The prosthetic mold system of claim 29, wherein the exterior dimension is a stem portion width and the interior dimension is an interior cavity width.

32. The prosthetic mold system of claim 29, further comprising a plurality of head molds, each one of the plurality of head molds having a concave arcuate interior surface defining an upper portion of a head cavity and configured to be attached to any one of the plurality of stem molds.

33. The prosthetic mold system of claim 32, wherein the head mold exterior includes at least one dimension that is substantially the same for each one of the plurality of head molds, and the head cavity includes at least one dimension that is different for each one of the plurality of head molds.

\* \* \* \* \*